United States Patent
Bauer et al.

(10) Patent No.: US 7,446,140 B2
(45) Date of Patent: Nov. 4, 2008

(54) DIALKYLPHOSPHINIC SALTS, THEIR USE, AND A PROCESS FOR THEIR PREPARATION

(75) Inventors: Harald Bauer, Kerpen (DE); Werner Krause, Huerth (DE); Martin Sicken, Cologne (DE); Norbert Weferling, Huerth (DE)

(73) Assignee: Clariant Produkte (Deutschland) GmbH, Sulzbach (DE)

( * ) Notice: Subject to any disclaimer, the term of this patent is extended or adjusted under 35 U.S.C. 154(b) by 397 days.

(21) Appl. No.: 11/126,981

(22) Filed: May 11, 2005

(65) Prior Publication Data
US 2006/0084734 A1  Apr. 20, 2006

(30) Foreign Application Priority Data
May 11, 2004  (DE) .................. 10 2004 023 085

(51) Int. Cl.
C08K 5/5313 (2006.01)
(52) U.S. Cl. ..................... 524/126; 524/133; 562/8
(58) Field of Classification Search .............. 524/126, 524/133; 562/8
See application file for complete search history.

(56) References Cited

U.S. PATENT DOCUMENTS

| | | | |
|---|---|---|---|
| 3,197,436 A | 7/1965 | Bueten et al. | |
| 3,255,125 A | 6/1966 | Bueton et al. | |
| 3,415,762 A | 12/1968 | Bueton et al. | |
| 5,869,722 A | 2/1999 | Kleiner | |
| 6,136,973 A | 10/2000 | Suzuki et al. | |
| 6,184,405 B1 | 2/2001 | Kleiner et al. | |
| 6,207,736 B1 | 3/2001 | Nass et al. | |
| 6,255,371 B1 | 7/2001 | Schlosser et al. | |
| 6,270,560 B1 | 8/2001 | Kleiner et al. | |
| 6,355,832 B1 | 3/2002 | Weferling et al. | |
| 6,359,171 B1 | 3/2002 | Weferling et al. | |
| 6,365,071 B1 | 4/2002 | Jenewein et al. | |
| 6,534,673 B1 | 3/2003 | Weferling et al. | |
| 6,547,992 B1 | 4/2003 | Schlosser et al. | |
| 7,087,666 B2 | 8/2006 | Hoerold et al. | |
| 2005/0009941 A1 | 1/2005 | Sicken et al. | |
| 2007/0072967 A1 | 3/2007 | Nass et al. | |

FOREIGN PATENT DOCUMENTS

| DE | 2827867 | 1/1980 |
|---|---|---|
| DE | 19616025 | 4/1997 |
| DE | 19614424 | 10/1997 |
| DE | 19645125 | 5/1998 |
| DE | 19734437 | 2/1999 |
| DE | 19851729 | 5/2000 |
| DE | 19910232 | 7/2000 |
| DE | 19933901 | 2/2001 |
| DE | 10241373 | 3/2004 |
| DE | 10323116 | 12/2004 |
| EP | 1024167 | 8/2000 |
| EP | 1055676 | 11/2000 |
| WO | WO 96/16948 | 6/1996 |
| WO | WO 98/08898 | 5/1998 |
| WO | WO 98/39306 | 9/1998 |
| WO | WO 98/45364 | 10/1998 |
| WO | WO 98/39381 | 11/1998 |
| WO | WO 99/28327 | 6/1999 |

OTHER PUBLICATIONS

German Search Report for DE 10 2004023085.4, Jan. 18, 2005.
U.S. Appl. No. 11/388,329, by Bauer et al., filed Mar. 24, 2006.
EPO Search Report for EP 05009647, mailed Mar. 29, 2006.
Drinkard, "Some Salts of Synmmetric Phosphinic Acids" Journal of The American Chemical Society Bd. 74, No. 21; XP002093391, pp. 5520, 5521 (Nov. 1952).
US 6,248,921, 06/2001, Weferling (withdrawn)

*Primary Examiner*—Peter Szekely
(74) *Attorney, Agent, or Firm*—Anthony A. Bisulca

(57) ABSTRACT

The invention relates to diorganylphosphinic salts of the formula (I) and/or diorganyldiphosphinic salts of the formula (II) and/or any of their polymers

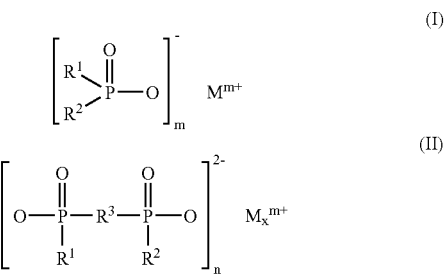

where
$R^1$ and $R^2$ are identical or different and are $C_1$-$C_6$-alkyl, linear or branched, and/or aryl;
$R^3$ is $C_1$-$C_{10}$-alkylene, linear or branched, $C_6$-$C_{10}$-arylene, -alkylarylene, or -arylalkylene;
M is Mg, Ca, Al, Sb, Sn, Ge, Ti, Fe, Zr, Zn, Ce, Bi, Sr, Mn, Li, Na, K, and/or a protonated nitrogen base;
m is from 1 to 4;
n is from 1 to 4;
x is from 1 to 4,
wherein the total content of partially water-soluble, ionizable compounds and the water-soluble content of the partially water-soluble, ionizable compounds is from 8200 to 100 ppm, preferably from 7000 to 200 ppm.

57 Claims, No Drawings

DIALKYLPHOSPHINIC SALTS, THEIR USE, AND A PROCESS FOR THEIR PREPARATION

The present invention is described in the German Priority application No. 102004023085.4, filed May 11, 2004, which is hereby incorporated by reference as is fully disclosed herein.

The invention relates to diorganylphosphinic salts, their use, and a process for their preparation.

U.S. Pat. Nos. 3,197,436, 3,255,125, and 3,415,762 describe poly(metal phosphinates) and their preparation.

DE-A-196 16 025 describes a process for preparation of a phosphinic salt from aluminum chloride and ethyl ethylmethylphosphinate.

DE-A-199 10 232 describes a process for preparation of a phosphinic salt, which comprises reacting phosphinic acids with aluminum oxide hydroxide.

DE-A-198 51 729 describes a process for preparation of a phosphinic salt, which comprises reacting sodium diethylphospinate in acetic acid with aluminum hydroxide.

WO-99/28327 describes a process for preparation of a phosphinic salt, which comprises freeing the diethylphosphinate from acetic acid and dissolving it in water. The aluminum salt is formed via addition of an aqueous aluminum sulfate solution, isolated in precipitated form, washed, and dried.

A disadvantage of the prior art is that the constitution of the diorganylphosphinic salts prepared in accordance therewith makes them insufficiently compatible with the polymers in which they are to be used.

It was therefore an object to provide diorganylphosphinic salts whose specific constitution gives them improved compatibility with the polymers.

A further object consisted in providing flame retardant compositions based on the inventive diorganylphosphinic salts, and flame-retardant polymer molding compositions based on diorganylphosphinic salts or, respectively, flame retardant compositions, and also flame-retardant polymer moldings with improved mechanical properties.

Surprisingly, it has now been found that the content of partially water-soluble, ionizable compounds has a decisive effect on compatibility with the polymer, or that a non-inventive content of partially water-soluble, ionizable compounds can lead to lack of adequate compatibility of diorganylphosphinic salts or, respectively, flame retardant compositions and polymer.

The invention achieves the abovementioned object via diorganylphosphinic salts with a specific content of partially water-soluble, ionizable compounds.

The invention therefore provides diorganylphosphinic salts of the formula (I) and/or diorganyldiphosphinic salts of the formula (II) and/or any of their polymers

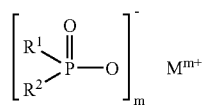
(I)

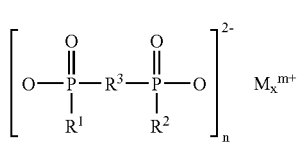
(II)

where
$R^1$ and $R^2$ are identical or different and are $C_1$-$C_6$-alkyl, linear or branched, and/or aryl;
$R^3$ is $C_1$-$C_{10}$-alkylene, linear or branched, $C_6$-$C_{10}$-arylene, -alkylarylene, or -arylalkylene;
M is Mg, Ca, Al, Sb, Sn, Ge, Ti, Fe, Zr, Zn, Ce, Bi, Sr, Mn, Li, Na, K, and/or a protonated nitrogen base;
m is from 1 to 4;
n is from 1 to 4;
x is from 1 to 4, wherein the total content of partially water-soluble, ionizable compounds and the water-soluble content of the partially water-soluble, ionizable compounds is from 8200 to 100 ppm, preferably from 7000 to 200 ppm.

All of the abovementioned compounds are ionizable and are composed of a water-soluble fraction (of, for example, salt, which can be dissolved out from the entire content of the abovementioned compounds) and of a non-water-soluble fraction (e.g. a salt fraction which partially forms a residue and is therefore insoluble).

The term "diorganylphosphinic salts" below includes not only the diorganylphosphinic salts themselves but also the diorganyldiphosphinic salts and their polymers.

Protonated nitrogen bases are preferably the protonated forms of ammonia or of primary, secondary, tertiary, or quaternary amines.

Protonated nitrogen bases are preferably the protonated forms of melamine, urea, biuret, guanidine, alkylguanidine, arylguanidine, diphenylguanidine, biguanide, biuret, allantoin, acetoguanamine, benzoguanamine, tolyltriazole, benzotriazole, 2-amino-4-methylpyrimidine, benzylurea, ethylenedimelamine, acetyleneurea, hydantoin, malonamide amidine, dimethylurea, 5,5-diphenylhydantoin, N,N'-diphenylurea, ethylenebis-5-triasection, glycine anhydride, tetramethylurea, triethanolamine, condensates of melamine, e.g. melem, melam, or melon, or higher-condensation-level compounds of this type.

The water-soluble content of the partially water-soluble, ionizable compounds is preferably from 3200 to 10 ppm, preferably from 2000 to 40 ppm.

The partially water-soluble, ionizable compounds preferably comprise compounds which derive from acetates, from chlorides, from nitrates, from sulfates, from phosphites, or from phosphates.

The total content of acetate (partially water-soluble, ionizable compound) is preferably from 2800 to 100 ppm, preferably from 2000 to 200 ppm, and the content of water-soluble acetate (water-soluble content of the partially water-soluble, ionizable compound) is preferably from 1100 to 10 ppm, preferably from 800 to 40 ppm.

The total content of chloride (partially water-soluble, ionizable compound) is preferably from 1700 to 100 ppm, preferably from 1500 to 200 ppm, and the content of water-soluble chloride (water-soluble content of the partially water-soluble, ionizable compound) is preferably from 950 to 10 ppm, preferably from 750 to 40 ppm.

The total content of nitrate (partially water-soluble, ionizable compound) is preferably from 2100 to 100 ppm, preferably from 900 to 150 ppm, and the content of water-soluble nitrate (water-soluble content of the partially water-soluble, ionizable compound) is preferably from 1100 to 10 ppm, preferably from 500 to 30 ppm.

The total content of phosphite (partially water-soluble, ionizable compound) is preferably from 8200 to 500 ppm, preferably from 7000 to 1000 ppm, and the content of water-soluble phosphite (water-soluble content of the partially water-soluble, ionizable compound) is preferably from 3000 to 50 ppm, preferably from 1800 to 100 ppm.

The total content of sulfate (partially water-soluble, ionizable compound) is preferably from 3800 to 100 ppm, preferably from 2500 to 200 ppm, and particularly preferably from 1000 to 300 ppm, and the content of water-soluble sulfate (water-soluble content of the partially water-soluble, ionizable compound) is preferably from 1200 to 10 ppm, preferably from 750 to 50 ppm.

The total content of phosphate (partially water-soluble, ionizable compound) is preferably from 7000 to 500 ppm, preferably from 5000 to 1000 ppm, and the content of water-soluble phosphate (water-soluble content of the partially water-soluble, ionizable compound) is preferably from 3000 to 50 ppm, preferably from 2000 to 100 ppm.

M is preferably aluminum, calcium, titanium, zinc, tin, or zirconium.

$R^1$ and $R^2$, identical or different, are preferably methyl, ethyl, n-propyl, isopropyl, n-butyl, tert-butyl, n-pentyl, and/or phenyl.

$R^3$ is preferably methylene, ethylene, n-propylene, isopropylene, n-butylene, tert-butylene, n-pentylene, n-octylene, n-dodecylene, phenylene, naphthylene, methylphenylene, ethylphenylene, tert-butylphenylene, methylnaphthylene, ethylnaphthylene, tert-butylnaphthylene, phenylmethylene, phenylethylene, phenylpropylene, or phenylbutylene.

The diorganylphosphinic salts of the formula (I) preferably comprise those from the group of aluminum trisdiethylphosphinate, aluminum trismethylethylphosphinate, aluminum trisdiphenylphosphinate, zinc bisdiethylphosphinate, zinc bismethylethylphosphinate, zinc bisdiphenylphosphinate, titanyl bisdiethylphosphinate, titanium tetrakisdiethylphosphinate, titanyl bismethylethylphosphinate, titanium tetrakismethylethylphosphinate, titanyl bisdiphenylphosphinate, titanium tetrakisdiphenylphosphinate and any desired mixture thereof.

The residual moisture level of the inventive diorganylphosphinic salts is preferably from 0.01 to 10% by weight, preferably from 0.1 to 1% by weight.

The particle size of the inventive diorganylphosphinic salt is preferably from 0.1 to 1000 μm, preferably from 1 to 100 μm.

The bulk density of the inventive diorganylphosphinic salts is preferably from 80 to 800 g/l, preferably from 200 to 700 g/l.

The solubility of the inventive diorganylphosphinic salts in water and/or in organic solvents, such as alcohols, glycols, aliphatic hydrocarbons, alicyclic hydrocarbons, aromatic hydrocarbons, halogenated hydrocarbons, ethers, glycol ethers, ketones, esters, and/or carboxylic acids is preferably from 0.001 to 10% by weight.

The invention also provides a process for preparation of diorganylphosphinic salts of the formula (I) and/or diorganyldiphosphinic salts of the formula (II), and/or their polymers, which comprises reacting the diorganylphosphinic acid with a free base, or b) with the elemental metal of the desired cation, or c) in its alkali metal salt form, with a salt of the desired cation, or d) in the form of a reactive derivative, with a derivative of the desired cation for from 0.01 to 1 hours at from 0 to 300° C.

The free bases preferably comprise the nitrogen bases as described under "protonated nitrogen bases", but in the unprotonated form.

The free base preferably comprises an oxide, mixed metal oxide hydroxide, hydroxide, carbonate, hydroxide carbonate, or hydrogencarbonate of the desired cation.

The desired cations preferably comprise Mg, Ca, Al, Sb, Sn, Ge, Ti, Fe, Zr, Zn, Ce, Bi, Sr, Mn, Li, Na, and/or K, in particular Al, Ca, Ti, Zn, Sn or Zr.

The salt of the desired cation preferably comprises compounds having inorganic anions of the seventh main group of the periodic system of the elements (halides), e.g. fluorides, chlorides, bromides, iodides; having anions of the oxo acids of the seventh main group (hypohalites, halites, halates, for example iodate, perhalates, for example perchlorate); having anions of the sixth main group (chalcogenides), e.g. oxides, hydroxides, peroxides, superoxides; having anions of the oxo acids of the sixth main group (sulfates, hydrogensulfates, sulfate hydrates, sulfites, peroxosulfates); having anions of the fifth main group (pnicogenides), e.g. nitrides, phosphides; having anions of the oxo acids of the fifth main group (nitrate, nitrate hydrates, nitrites, phosphates, peroxophosphates, phosphites, hypophosphites, pyrophosphates); having anions of the oxo acids of the fourth main group (carbonates, hydrogencarbonates, hydroxide carbonates, carbonate hydrates, silicates, hexafluorosilicates, hexafluorosilicate hydrates, stannates); having anions of the oxo acids of the third main group (borates, polyborates, peroxoborates); having anions of the pseudohalides (thiocyanates, cyanates, cyanides); having anions of the oxo acids of the transition metals (chromates, chromites, molybdates, permanganate).

Further preferred salts of the desired cation are compounds having organic anions from the group of the mono-, di-, oligo-, or polycarboxylic acids (salts of formic acid (formates), of acetic acid (acetates, acetate hydrates), of trifluoroacetic acid (trifluoroacetate hydrates), propionates, butyrates, valerates, caprylates, oleates, stearates, of oxalic acid (oxalates), of tartaric acid (tartrates), citric acid (citrates, basic citrates, citrate hydrates), benzoic acid (benzoates), salicylates, lactic acid (lactate, lactate hydrates), acrylic acid, maleic acid, succinic acid, of amino acids (glycine), of acidic hydroxy functions (phenolates etc.), para-phenolsulfonates, para-phenolsulfonate hydrates, acetylacetonate hydrates, tannates, dimethyldithiocarbamates, trifluoromethanesulfonate, alkylsulfonates, aralkylsulfonates.

Further preferred salts of the desired cation are compounds having anions from the group of the monoorganylphosphinates such as mono($C_{1-18}$-alkyl)phosphinates, mono($C_6$-$C_{10}$-aryl)phosphinates, mono($C_{1-18}$-aralkyl)phosphinates, e.g. monomethylphosphinates, monoethylphosphinates, monobutylphosphinates, monohexylphosphinates, monophenylphosphinates, monobenzylphosphinates, etc.

Further preferred salts of the desired cation are compounds having anions from the group of the monoorganylphosphonates such as mono($C_{1-18}$-alkyl)phosphonates, mono($C_6$-$C_{10}$-aryl)phosphonates, mono($C_{1-18}$-aralkyl)phosphonates, e.g. monomethylphosphonates, monoethylphosphonates, monobutylphosphonates, monohexylphosphonates, monophenylphosphonates, monobenzylphosphonates, etc.

The salt of the desired cation preferably comprises salts of protonated nitrogen bases, e.g. those of ammonia, primary, secondary, tertiary, and quaternary amines.

The salt of the desired cation preferably comprises salts of protonated nitrogen bases e.g. those of melamine, urea, biuret, guanidine, alkylguanidine, arylguanidine, diphenylguanidine, biguanide, biuret, allantoin, acetoguanamine, benzoguanamine, tolyltriazole, benzotriazole, 2-amino-4-methylpyrimidine, benzylurea, ethylenedimelamine, acetyleneurea, hydantoin, malonamide amidine, dimethylurea, 5,5-diphenylhydantoin, N,N'-diphenylurea, ethylenebis-5- triasection, glycine anhydride, tetramethylurea, triethanolamine, condensates of melamine, e.g. melem, melam, or melon, or higher-condensation-level compounds of this type.

The reactive derivatives preferably comprise diorganylphosphinic esters, diorganylphosphinic pyroesters, diorganylphosphinic chlorides, diorganylphosphinic phosphates, diorganylphosphinic acetates, diorganylphosphinic phenolates, and/or other derivatives.

In the inventive process, the diorganylphosphinic salt is preferably freed from ancilliary components via washing with wash solvents, and the ancilliary components are preferably removed by means of solid-liquid separation.

The invention also provides the use of the inventive diorganylphosphinic salts as flame retardants, in particular in polymers or in flame retardant compositions, in particular for polymers.

In this use, the flame retardant composition preferably comprises from 50 to 99.9% by weight of the inventive diorganylphosphinic salt and from 0.1 to 50% by weight of at least one additive.

In this use, the flame retardant composition particularly preferably comprises from 95 to 70% by weight of the inventive diorganylphosphinic salt and from 5 to 30% by weight of at least one additive.

In the use of a flame retardant composition, the additives preferably derive from the group of melamine phosphate, dimelamine phosphate, pentamelamine triphosphate, trimelamine diphosphate, tetrakismelamine triphosphate, hexakismelamine pentaphosphate, melamine diphosphate, melamine tetraphosphate, melamine pyrophosphate, melamine polyphosphate, melam polyphosphate, melem polyphosphate, and/or melon polyphosphate.

In the use of a flame retardant composition, the additives preferably derive from the group of oligomeric esters of tris(hydroxyethyl) isocyanurate with aromatic polycarboxylic acids, benzoguanamine, tris(hydroxyethyl) isocyanurate, allantoin, glycoluril, melamine, melamine cyanurate, urea cyanurate, dicyandiamide, and/or guanidine.

In the use of a flame retardant composition, the additives preferably derive from the group of the zinc compounds, such as zinc oxide, zinc hydroxide, zinc oxide hydrate, zinc carbonate, zinc stannate, zinc hydroxystannate, zinc silicate, zinc phosphate, zinc borate, zinc molybdate.

In the use of a flame retardant composition, the additives preferably derive from the group of the carbodiimides and/or (poly)isocyanates, e.g. carbonylbiscaprolactam and/or styrene-acrylic polymers.

In the abovementioned use, the average particle size of the flame retardant composition is preferably from 0.1 to 3000 μm, preferably from 0.1 to 1000 μm, and in particular from 1 to 100 μm.

In the abovementioned use, the residual moisture level of the flame retardant composition is preferably from 0.01 to 10% by weight, preferably from 0.1 to 1% by weight.

The invention also provides the use of the inventive diorganylphosphinic salts in or for production of flame-retardant polymer molding compositions.

In this use, the flame-retardant polymer molding composition preferably comprises from 1 to 50% by weight of inventive diorganylphosphinic salts, and from 1 to 99% by weight of polymer or a mixture of these.

In this use, the flame-retardant polymer molding composition preferably comprises from 1 to 50% by weight of inventive diorganylphosphinic salts, from 1 to 99% by weight of polymer or a mixture of these, and from 0.1 to 60% by weight of additives.

In this use, the flame-retardant polymer molding composition preferably comprises from 5 to 30% by weight of inventive diorganylphosphinic salts, from 5 to 90% by weight of polymer or a mixture of these, and from 5 to 40% by weight of additives.

The polymers here preferably derive from the group of the thermoplastic polymers, such as polyester, polystyrene, or polyamide, and/or of the thermoset polymers.

The polymer molding composition here preferably has the shape of a cylinder with a circular, elliptical, or irregular base, or of a sphere, cushion, cube, parallelepiped, or prism, the length:diameter ratio being from 1:50 to 50:1, preferably from 1:5 to 5:1.

In this use, the polymer molding composition is preferably obtained by mixing the diorganylphosphinic salts and/or the flame retardant compositions with the polymer pellets and optionally with additives in a mixer, homogenizing them in a compounding assembly at relatively high temperatures in the polymer melt, and then drawing the homogenized polymer strand off, and cooling it and dividing it.

In this use, the compounding assembly preferably derives from the group of the single-screw extruders, multisection screws, or twin-screw extruders.

The invention also provides the use of the inventive diorganylphosphinic salts in flame-retardant polymer moldings, in flame-retardant polymer films, in flame-retardant polymer filaments, or in flame-retardant polymer fibers.

In this use, the flame-retardant polymer moldings, flame-retardant polymer films, flame-retardant polymer filaments, or flame-retardant polymer fibers preferably comprise from 1 to 50% by weight of inventive diorganylphosphinic salts, from 1 to 99% by weight of polymer or of a mixture of these, from 0 to 60% by weight of additives, and from 0 to 60% by weight of filler or of reinforcing materials.

In this use, the flame-retardant polymer moldings, flame-retardant polymer films, flame-retardant polymer filaments, or flame-retardant polymer fibers preferably comprise from 1 to 50% by weight of inventive diorganylphosphinic salts, from 1 to 99% by weight of polymer or of a mixture of these, from 0.1 to 60% by weight of additives, and from 0.1 to 60% by weight of filler or of reinforcing materials.

In this use, the flame-retardant polymer moldings, flame-retardant polymer films, flame-retardant polymer filaments, or flame-retardant polymer fibers preferably comprise from 1 to 70% by weight of inventive flame retardant composition, from 1 to 99% by weight of polymer or of a mixture of these, from 0.1 to 60% by weight of additives, and from 0.1 to 60% by weight of filler or of reinforcing materials.

In this use, the flame-retardant polymer moldings, flame-retardant polymer films, flame-retardant polymer filaments, or flame-retardant polymer fibers preferably comprise from 1 to 70% by weight of inventive flame-retardant polymer molding composition, from 1 to 99% by weight of polymer or of a mixture of these, from 0.1 to 60% by weight of additives, and from 0.1 to 60% by weight of filler or of reinforcing materials.

In the processes for preparation of the abovementioned polymer molding compositions, the preferred processing temperatures for polystyrene are from 170 to 200° C., for polypropylene are from 200 to 300° C., for polyethylene terephthalate (PET) are from 250 to 290° C., for polybutylene terephthalate (PBT) are from 230 to 270° C., for nylon-6 (PA 6) are from 260 to 290° C., for nylon-6,6 (PA 6.6) are from 260 to 290° C., and for polycarbonate are from 280 to 320° C.

Effective screw lengths (L) of the extruder in this process, expressed as a multiple of the screw diameter (D) are preferably from 4 to 200D, preferably from 10 to 50D.

In the process for the production of flame-retardant polymer moldings, it is preferable to process a flame-retardant polymer molding composition via injection molding and compression molding, foam injection molding, internal gas pressure injection molding, blowmolding, film casting, calendering, laminating, coating, etc. to give the flame-retardant polymer molding.

In the abovementioned process, the processing temperatures for polystyrene are from 200 to 250° C., for polypropylene are from 200 to 300° C., for polyethylene terephthalate (PET) are from 250 to 290° C., for polybutylene terephthalate (PBT) are from 230 to 270° C., for nylon-6 (PA 6) are from 260 to 290° C., for nylon-6,6 (PA 6.6) are from 260 to 290° C., and for polycarbonate are from 280 to 320° C.

One factor which can express the compatibility of an additive with a polymer is the extent to which the average molecular weight is reduced by the additive during the processing of a polymer. To this end, a parameter characteristic of the average molecular weight of the untreated polymer is compared with the parameter for the additive-treated polymer.

One such dimensionless parameter is the specific viscosity (SV value). This derives from the determination of the viscosity of a solution of the polymer in a solvent, the viscosity of the polymer solution here being used to form a ratio to the viscosity of the pure solvent.

The SV value is used to express compatibility. Accordingly, compatibility (SV value), for example with polybutylene terephthalate, shows a sudden improvement beginning at a certain content of partially water-soluble ionizable compounds.

In the case of polybutylene terephthalate, SV values of from 750 to 1400 are preferred by the invention, particularly preferred values being from 850 to 1250. The SV value may be determined from an inventive polymer molding composition or from a polymer molding.

Volume flow index (melt flow index, MFI, MVR) can also be utilized for assessment of compatibility. A marked rise in MVR value indicates polymer degradation.

In the case of inventive glass-fiber-reinforced flame-retardant polymer molding compositions based on nylon-6,6, the value is from 2 to 200 cm$^3$/min (275° C., 5 kg).

Examples of the partially water-soluble, ionizable compounds are substances from the group of the inorganic and organic, and also in particular organophosphorus, salts and mixtures thereof.

Preference is given to partially water-soluble, ionizable compounds having inorganic anions of the seventh main group (halides), e.g. fluorides, chlorides, bromides, iodides; having anions of the oxo acids of the seventh main group (hypohalites, halites, halates, e.g. iodate, perhalates, e.g. perchlorate); having anions of the sixth main group (chalcogenides), e.g. oxides, hydroxides, peroxides, superoxides; having anions of the oxo acids of the sixth main group (sulfates, hydrogensulfates, sulfate hydrates, sulfites, peroxosulfates); having anions of the fifth main group (pnicogenides), e.g. nitrides, phosphides; having anions of the oxo acids of the fifth main group (nitrate, nitrate hydrates, nitrites, phosphates, peroxophosphates, phosphites, hypophosphites, pyrophosphates); having anions of the oxo acids of the fourth main group (carbonates, hydrogencarbonates, hydroxide carbonates, carbonate hydrates, silicates, hexafluorosilicates, hexafluorosilicate hydrates, stannates); having anions of the oxo acids of the third main group (borates, polyborates, peroxoborates); having anions of the pseudohalides (thiocyanates, cyanates, cyanides); having anions of the oxo acids of the transition metals (chromates, chromites, molybdates, permanganate).

Preference is also given to partially water-soluble, ionizable compounds having organic anions from the group of the mono-, di-, oligo-, or polycarboxylic acids (salts of formic acid (formates), of acetic acid (acetates, acetate hydrates), of trifluoroacetic acid (trifluoroacetate hydrates), propionates, butyrates, valerates, caprylates, oleates, stearates, of oxalic acid (oxalates), of tartaric acid (tartrates), citric acid (citrates, basic citrates, citrate hydrates), benzoic acid (benzoates), salicylates, lactic acid (lactate, lactate hydrates), acrylic acid, maleic acid, succinic acid, of amino acids (glycine), of acidic hydroxy functions (phenolates etc.), para-phenolsulfonates, para-phenolsulfonate hydrates, acetylacetonate hydrates, tannates, dimethyldithiocarbamates, trifluoromethanesulfonate, alkylsulfonates, aralkylsulfonates.

Preference is also given to partially water-soluble, ionizable compounds having anions from the group of the monoorganylphosphinates such as mono($C_{1-18}$-alkyl)phosphinates, mono($C_6$-$C_{10}$-aryl)phosphinates, mono($C_{1-18}$-aralkyl)phosphinates, e.g. monomethylphosphinates, monoethylphosphinates, monobutylphosphinates, monohexylphosphinates, monophenylphosphinates, monobenzylphosphinates, etc.

Preference is also given to partially water-soluble, ionizable compounds having anions from the group of the monoorganylphosphonates such as mono($C_{1-18}$-alkyl)phosphonates, mono($C_6$-$C_{10}$-aryl)phosphonates, mono($C_{1-18}$-aralkyl)phosphonates, e.g. monomethylphosphonates, monoethylphosphonates, monobutylphosphonates, monohexylphosphonates, monophenylphosphonates, monobenzylphosphonates, etc.

The invention can also use any desired mixtures.

Preference is given to partially water-soluble, ionizable compounds having cations of the alkali metals, or else having cations of protonated nitrogen bases, e.g. those of ammonia, primary, secondary, tertiary, and quaternary amines.

Preference is given to partially water-soluble, ionizable compounds having cations of protonated nitrogen bases, e.g. those of melamine, urea, biuret, guanidine, alkylguanidine, arylguanidine, diphenylguanidine, biguanide, biuret, allantoin, acetoguanamine, benzoguanamine, tolyltriazole, benzotriazole, 2-amino-4-methylpyrimidine, benzylurea, ethylenedimelamine, acetyleneurea, hydantoin, malonamide amidine, dimethylurea, 5,5-diphenylhydantoin, N,N'-diphenylurea, ethylenebis-5-triazone, glycine anhydride, tetramethylurea, triethanolamine, condensates of melamine, e.g. melem, melam, or melon, or higher-condensation-level compounds of this type.

Preference is given to partially water-soluble, ionizable compounds having cations of the alkaline earth metals; having cations of the elements of the third main group; having cations of the transition group elements. Particularly preferred transition group elements here are titanium, iron, zinc. Any desired mixtures are also in accordance with the invention.

The content of partially ionizable compounds is a consequence of the method of preparation of the diorganylphosphinic salt. Examples of sources can be the solvent and/or the starting compounds.

The content of partially ionizable compounds here has to be carefully considered. Firstly, the entire content present in the metal diorganylphosphinate is important (total content). Total contents of from 8200 to 100 ppm are preferred, particularly from 7000 to 200 ppm.

Surprisingly, it has now been found that only a portion of the ionizable compounds can be removed from the diorganylphosphinic salt via aqueous extraction (water-soluble fraction of ionizable compounds). The residue, i.e. the difference between total content of partially ionizable compounds and water-soluble content of ionizable compounds, is not extractable from the diorganylphosphinic salt, even via repeated leaching. Because the present diorganylphosphinic salts comprise polymeric coordination compounds, anions may have been bonded in the form of metal phosphinates, metal hydroxophosphinates, or metal hydroxo salts.

Preferred contents of water-soluble ionizable compounds are from 3200 to 10 ppm, and particularly from 200 to 40 ppm.

Particle size above the preferred range makes uniform dispersion of the inventive diorganylphosphinic salts more difficult, and particle size below the preferred range makes incorporation more difficult, because dusting and explosion risk increase.

Residual moisture levels above the preferred ranges of the invention cause increased polymer degradation.

The inventive aluminum trisdiethylphosphinate undergoes a reversible change in crystalline state (X-ray powder data) at from 160 to 200° C., preferably from 175 to 185° C. This type of change can be advantageous during processing with plastics.

The inventive diorganylphosphinic salts have a preferred content of initiator end groups: from 0.0001 to 10 mol %, particularly from 0.001 to 1 mol %. Initiator end groups can remain bonded to the final molecule of the free-radical chain during free-radical chain termination, during formation of the adduct of the olefin with the hypophosphite.

The preferred L color values of the inventive diorganylphosphinic salts are from 85 to 99.9, particularly from 90 to 98. Diorganylphosphinic salts with L values below the inventive range require greater use of white pigment. This impairs the mechanical stability properties of the polymer molding (e.g. modulus of elasticity).

Preferred a color values of the inventive diorganylphosphinic salts are from −4 to +9, particularly from −2 to +6.

Preferred b color values of the inventive diorganylphosphinic salts are from −2 to +6, particularly from −1 to +3.

The color values stated are Hunter system values (CIE-LAB system, Commission Internationale d'Eclairage). L values range from 0 (black) to 100 (white), a values range from −a (green) to +a (red), and b values range from −b (blue) to +b (yellow).

Diorganylphosphinic salts with a or b values outside the inventive range require greater use of white pigment. This impairs the mechanical stability properties of the polymer molding (e.g. modulus of elasticity).

The inventive diorganylphosphinic salts exhibit improved compatibility with a wide variety of polymers used in inventive flame-retardant polymer molding compositions or in inventive flame-retardant polymer moldings, e.g. in polyolefins, polystyrenes and polystyrene copolymers, polyacrylates and polymethacrylates, vinyl and allyl polymers, homo- and copolymers of unsaturated alcohols, polyacetals, polyphenylene sulfides, polyamides and copolyamides, polyesters, polycarbonates.

Process

The invention prepares the diorganylphosphinic salt by reacting the diorganylphosphinic acid with elemental metal or with a metal salt for from 0.01 to 1 hour at from 0 to 300° C. Preferred metal salts here are metal oxides, mixed metal oxide hydroxides, hydroxides, etc.

Another inventive embodiment prepares the diorganylphosphinic salt by reacting the diorganylphosphinic acid with a free base for from 0.01 to 1 hour at from 0 to 300° C.

Another embodiment prepares the inventive diorganylphosphinic salt by reacting the diorganylphosphinic acid in the form of an alkali metal salt with a salt of the desired cation for from 0.01 to 1 hour at from 0 to 300° C.

Preferred salts which supply the desired cations here are acetates, hydroxoacetates, chlorides, hydroxochlorides, nitrates, sulfates, hydroxosulfates. Their concentration in the aqueous solution is preferably from 5 to 95% (anhydrous solid), particularly preferably from 20 to 50% by weight.

The invention prefers the alkali metal diorganylphosphinic salts in anhydrous, hydrated, or dissolved form.

The preferred solubility of the inventive alkali metal diorganylphosphinic salts in water and/or in the usual organic solvents is from 1 to 70% by weight (anhydrous solid).

The preferred solubility of the inventive diorganylphosphinic salts of the desired cation in water and/or in the usual organic solvents is from 0.001 to 10% by weight (anhydrous solid).

Another embodiment prepares the inventive diorganylphosphinic salts by reacting the diorganylphosphinic acid in the form of a reactive derivative with a derivative of the desired cation for from 0.01 to 1 hour at from 0 to 300° C. Preferred diorganylphosphinic derivatives are diorganylphosphinic esters, diorganylphosphinic pyroesters, diorganylphosphinic chlorides, diorganylphosphinic phosphates, diorganylphosphinic acetates, diorganylphosphinic phenolates, etc.

The reactions may optionally take place in a solvent system. Organic and inorganic solvents are preferred.

Among the organic solvents, preference is given to alcohols, oligoalcohols and polyalcohols, esters, and mono-, di-, oligo-, and polycarboxylic acids.

Among the inorganic solvents, preference is given to water. A pH of from 0 to 14 is preferred. One embodiment prefers a pH from 0.5 to 8.

Preferred containers and units for the reaction are mixers, mixer dryers, tanks, autoclaves, high-pressure stirred vessels, kneaders, extruders, roller compacters, etc.

The preferred atmospheric pressure during the reaction is from 0.001 to 100 MPa.

The inventive diorganylphosphinic salt is preferably freed from ancilliary components. The invention achieves this via washing with wash solvents which take up the ancilliary components, and removal of these. According to the invention, the washing takes place at from 0 to 300° C.

The removal takes place by the usual processes of solid-liquid separation. Preference is given to filtering, centrifuging, sedimenting, removal in a hydrocyclone, flotation.

The invention can use one or more stages to free the product from these materials. The ratio of wash solvent to solvent-free crude product here can preferably be from 0.1:1 to 10 000:1 (based on weight).

The invention removes residual wash solvent from the inventive diorganylphosphinic salt. This is achieved by the usual processes, e.g. removal via compression, centrifuging, drying, etc. The drying process takes place in one stage or in two or more stages, preferably at a pressure of from 10 Pa to 100 Mpa, for a period of from 0.01 to 1000 h and at a temperature of from −20 to +500° C., particularly preferably at from 50 to 350° C.

Inventive wash solvents are organic and inorganic solvents. Among the organic solvents, preference is given to alcohols, oligoalcohols and polyalcohols, esters, and mono-, di-, oligo-, and polycarboxylic acids. Among the inorganic solvents, preference is given to water. Preference is given to a pH of from 0 to 14. One embodiment prefers a pH of from 0.5 to 8.

The invention also provides the use of the inventive diorganylphosphinic salts in flame retardant compositions.

According to the invention, the preferred use for the inventive diorganylphosphinic salts is as flame retardant. According to the invention, the preferred use for the inventive diorganylphosphinic salts is in flame retardant compositions. For this, they are preferably used together with other additives.

The inventive flame retardant composition preferably comprises an inventive diorganylphosphinic salt.

The inventive flame retardant composition preferably comprises:
1) from 30 to 99.9% by weight of an inventive diorganylphosphinic salt
2) from 0.1 to 50% by weight of at least one additive.

The inventive flame retardant composition particularly preferably comprises from 95 to 70% by weight of an inventive diorganylphosphinic salt and from 5 to 30% of at least one additive.

Examples of preferred other additives in flame retardant compositions are synergists, as described in DE-A-28 27 867, DE-A-199 33 901, DE-A-196 14 424, DE-A-197 34 437.

Synergists used in the invention comprise melamine phosphate (e.g ®Melapur MP from Ciba-DSM Melapur), dimelamine phosphate, pentamelamine triphosphate, trimelamine diphosphate, tetrakismelamine triphosphate hexakismelamine pentaphosphate, melamine diphosphate, melamine tetraphosphate, melamine pyrophosphate (e.g. ®Budit 311 from Budenheim, ®MPP-B from Sanwa Chemicals), melamine polyphosphates, melam polyphosphates, melem polyphosphates, and/or melon polyphosphates, or a mixture of these. Particular preference is given to melamine polyphosphates, such as ®Melapur 200/70 from Ciba-DSM Melapur, ®Budit 3141, 3141 CA, and 3141 CB, and melamine polyphosphate/melamine pyrophosphate grades ®13-1100, 13-1105, 13-1115, ®MPP02-244 from Hummel-Croton, and ®PMP-200 from Nissan.

Another embodiment prefers condensates of melamine (e.g. melam, melem, and/or melon) or reaction products of melamine with phosphoric acid, or prefers reaction products of condensates of melamine with phosphoric acid, or else prefers any mixture of the products mentioned. Examples of condensates of melamine are melem, melam, or melon, or higher-condensation-level compounds of this type, and also mixtures of these, and can, by way of example, be prepared via the process described in WO-96/16948.

Reaction products with phosphoric acid are compounds which are produced via the reaction of melamine or of the condensed melamine compounds, such as melam, melem or melon, etc., with phosphoric acid. Examples of these are melamine polyphosphate, melam polyphosphate, and melem polyphosphate, and mixed polysalts as described in WO-98/39306. The compounds mentioned are known from the literature and can also be prepared by processes other than direct reaction with phosphoric acid. By way of example, melamine polyphosphate may be prepared by analogy to WO-98/45364 via reaction of polyphosphoric acid and melamine, or by analogy with WO-98/08898 via condensation of melamine phosphate or melamine pyrophosphate.

Other synergists preferred in the invention are oligomeric esters of tris(hydroxyethyl) isocyanurate with aromatic polycarboxylic acids, benzoguanamine, tris(hydroxyethyl) isocyanurate, allantoin, glycoluril, melamine, melamine condensates, such as melam, melem, and/or melon, melamine cyanurate (e.g. ®Melapur MC or ®Melapur MC XL from Ciba-DSM Melapur), dicyandiamide, and/or guanidine.

Other synergists preferred in the invention are nitrogen-containing phosphates of the formulae $(NH_4)yH_3-yPO_4$ and $(NH_4PO_3)z$, where y is from 1 to 3, and z is from 1 to 10 000.

Nitrogen compounds are preferred synergists in the invention, for example those of the formulae (III) to (VI II), or a mixture thereof

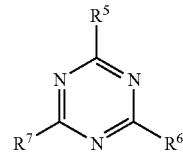
(III)

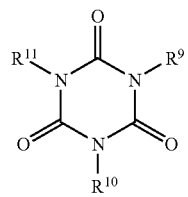
(IV)

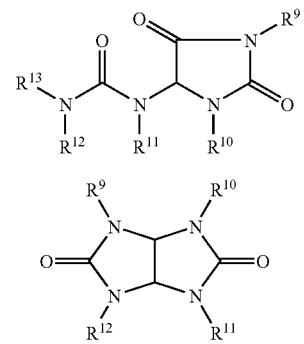
(V)

(VI)

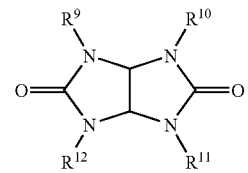
(VII)

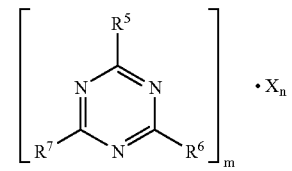
(VIII)

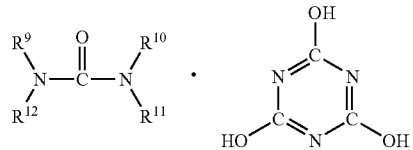

where
$R^5$ to $R^7$ are hydrogen, $C_1$-$C_8$-alkyl, $C_5$-$C_{16}$-cycloalkyl or -alkylcycloalkyl, optionally substituted with a hydroxy or a $C_1$-$C_4$-hydroxyalkyl function, $C_2$-$C_8$-alkenyl, $C_1$-$C_8$-alkoxy, -acyl, -acyloxy, $C_6$-$C_{12}$-aryl or -arylalkyl, —$OR^8$, or —$N(R^8)R^9$, including systems of alicyclic-N or aromatic-N type,
$R^8$ is hydrogen, $C_1$-$C_8$-alkyl, $C_5$-$C_{16}$-cycloalkyl or -alkylcycloalkyl, optionally substituted with a hydroxy or a $C_1$-$C_4$-hydroxyalkyl function, $C_2$-$C_8$-alkenyl, $C_1$-$C_8$-alkoxy, -acyl, -acyloxy, or $C_6$-$C_{12}$-aryl or -arylalkyl,
$R^9$ to $R^{13}$ are the same as the groups for $R^8$, or else —O—$R^8$,
m and n, independently of one another, are 1, 2, 3, or 4,
x is acids which can form adducts with triazine compounds (III).

Other preferred additives in flame retardant compositions are, for example as in EP-A-1 024 167, oxygen compounds of silicon, magnesium compounds, or, by way of example, metal carbonates of metals of the second main group of the Periodic Table, red phosphorus, zinc compounds, or aluminum compounds.

Other additives preferred in flame retardant compositions are oxides, hdyroxides, carbonates, silicates, borates, stannates, mixed oxide hydroxides, oxide hydroxide carbonates, hydroxide silicates, or hydroxide borates, or a mixture of these substances.

Other preferred additives in flame retardant compositions are magnesium compounds, e.g. magnesium oxide, magnesium hydroxide, hydrotalcites, dihydrotalcite, magnesium carbonates, or magnesium calcium carbonates.

Other preferred additives in flame retardant compositions are calcium compounds, e.g. calcium hydroxide, calcium oxide, hydrocalumite.

Other preferred additives in flame retardant compositions are zinc compounds, e.g. zinc oxide (e.g. active zinc oxide), zinc hydroxide, zinc oxide hydrate, zinc carbonate (e.g. basic zinc carbonate, anhydrous zinc carbonate), zinc stannate, zinc hydroxystannate, basic zinc silicate, basic zinc phosphate, basic zinc borate (e.g. ®Firebrake ZB or 415 from Borax), basic zinc molybdates (®Kemgard 911 B, ®Kemgard 911C from Sherwin-Williams Company), or basic zinc sulfides.

Other preferred additives in flame retardant compositions are aluminum compounds, e.g. aluminum oxide, aluminum hydroxide, boehmite, gibbsite, or aluminum phosphate; manganese compounds, e.g. manganese oxide, manganese hydroxide; tin compounds, e.g. tin oxide.

Other preferred additives in flame retardant compositions are described in DE-A-199 20 276, e.g. those of the carbodiimides group (e.g. ®Stabaxol P from BASF) and/or (poly) isocyanates (e.g. ®Basonat HI 100 or ®Vestanat T 1890/100).

Other preferred additives in flame retardant compositions are carbonylbiscaprolactam (Allinco) or styrene-acrylic polymers (®Joncryl ADR-4357 from Johnson).

Other preferred additives in flame retardant compositions come from the group of the sterically hindered phenols (e.g. ®Hostanox OSP 1, ®Tinuvin grades, ®Irganox grades, ®Irgafos grades, and ®Tinosorb grades), sterically hindered amines and light stabilizers (e.g. ®Chimasorb 944, (®Hostavin grades, and ®Tinuvin grades), phosphonites and antioxidants (e.g. Sandostab® P-EPQ from Clariant), and release agents (®Licomont grades from Clariant).

The inventive diorganylphosphinic salt is preferably used in flame-retardant formulations in further-processed form (coated, dust-reduced, melt-granulated and/or droplet-granulated, compacted, spray-granulated, dispersed, paste form, etc).

The average particle size of the inventive flame retardant compositions is from 0.1 to 3000 μm.

In one embodiment, the inventive flame retardant compositions have an average particle size of from 0.1 to 1000 μm, preferably from 1 to 100 μm.

In another embodiment, the inventive flame retardant compositions preferably have an average particle size of from 100 to 3000 μm, preferably from 200 to 2000 μm.

Particle size above the preferred range makes uniform dispersion of the inventive diorganyiphosphinic salt more difficult, and particle size below the preferred range makes incorporation more difficult because there is greater risk of dusting and explosion.

The preferred bulk density of the inventive flame retardant composition is from 80 to 1500 g/l, particularly preferably from 200 to 1000 g/l.

In one embodiment, the preferred bulk density of the inventive flame retardant composition is from 80 to 800 g/l, particularly preferably from 200 to 700 g/l.

In another embodiment, the preferred bulk density of the inventive flame retardant composition is from 200 to 1500 g/l, preferably from 300 to 1000 g/l.

The invention in particular provides the use of the inventive diorganylphosphinic salts and/or of the flame retardant compositions in flame-retardant polymer molding compositions comprising polymer. Preferred polymers of the invention are thermoplastic polymers, e.g. polyesters, polystyrene, or polyamide, and/or thermoset polymers.

The flame-retardant polymer molding composition preferably comprises from 1 to 50% by weight of inventive diorganylphosphinic salts, from 1 to 99% by weight of polymer or a mixture of these from 0 to 60% by weight of additives.

The flame-retardant polymer molding composition particularly preferably comprises
from 5 to 30% by weight of inventive diorganylphosphinic salts,
from 5 to 90% by weight of polymer or a mixture of these
from 5 to 40% by weight of additives.

The flame-retardant polymer molding composition particularly preferably comprises
from 5 to 30% by weight of inventive diorganylphosphinic salts,
from 5 to 90% by weight of polymer or a mixture of these
from 5 to 40% by weight of additives
from 5 to 40% by weight of filler or of reinforcing materials.

The flame-retardant polymer molding composition preferably comprises
from 1 to 50% by weight of inventive flame retardant compositions,
from 1 to 99% by weight of polymer or a mixture of these
from 0 to 60% by weight of additives.

The flame-retardant polymer molding composition particularly preferably comprises
from 5 to 30% by weight of inventive flame retardant compositions,
from 5 to 90% by weight of polymer or a mixture of these
from 5 to 40% by weight of additives.

The flame-retardant polymer molding composition particularly preferably comprises
from 5 to 30% by weight of inventive flame retardant compositions,
from 5 to 90% by weight of polymer or a mixture of these
from 5 to 40% by weight of additives
from 5 to 40% by weight of filler or of reinforcing materials.

The polymers preferably comprise polymers of mono- and diolefins, examples being polypropylene, polyisobutylene, poly-1-butene, poly-4-methyl-1-pentene, polyisoprene, or polybutadiene, or else polymers of cycloolefins, e.g. of cyclopentene or norbornene; and polyethylene (which may, if appropriate, have been crosslinked), e.g. high-density polyethylene (HDPE), high-density high-molecular-weight polyethylene (HDHMWPE), high-density ultrahigh-molecular-weight polyethylene (HDUHMWPE), medium-density polyethylene (MDPE), low-density polyethylene (LDPE), linear low-density polyethylene (LLDPE), branched low-density polyethylene (VLDPE), and mixtures thereof.

The polymers preferably comprise copolymers of mono- and diolefins with one another or with other vinyl monomers, examples being ethylene-propylene copolymers, linear low-density polyethylene (LLDPE), and its mixtures with low-density polyethylene (LDPE), propylene-1-butene copolymers, propylene-isobutylene copolymers, ethylene-1-butene copolymers, ethylene-hexene copolymers, ethylene-methylpentene copolymers, ethylene-heptene copolymers, ethylene-octene copolymers, propylene-butadiene copolymers, isobutylene-isoprene copolymers, ethylene-alkyl acrylate copolymers, ethylene-alkyl methacrylate copolymers, ethylene-vinyl acetate copolymers and their copolymers with carbon monoxide, or ethylene-acrylic acid copolymers and their salts (ionomers), and terpolymers of ethylene with propylene and with a diene, such as hexadiene, dicyclopentadiene, or ethylidenenorbornene; and mixtures of these copolymers with one another, e.g. polypropylene/ethylene-propylene copolymers, LDPE/ethylene-vinyl acetate copolymers, LDPE/ethylene-acrylic acid copolymers, LLDPE/ethylene-vinyl acetate copolymers, LLDPE/ethylene-acrylic acid copolymers, and alternating- or random-structure polyalkylene/carbon monoxide copolymers and their mixtures with other polymers, e.g. with polyamides.

The polymers preferably comprise hydrocarbon resins (e.g. $C_5$-$C_9$), inclusive of hydrogenated modifications thereof (e.g. tackifier resins), and mixtures of polyalkylenes and starch.

The polymers preferably comprise polystyrene (polystyrene 143E from BASF), poly(p-methylstyrene), poly(alpha-methylstyrene).

Polymers preferably comprise copolymers of styrene or alpha-methylstyrene with dienes or with acrylic derivatives, examples being styrene-butadiene, styrene-acrylonitrile, styrene-alkyl methacrylate, styrene-butadiene-alkyl acrylate, styrene-butadiene-alkyl methacrylate, styrene-maleic anhydride, styrene-acrylonitrile-methyl acrylate; high-impact-resistant mixtures composed of styrene copolymers and of another polymer, e.g. of a polyacrylate, of a diene polymer, or of an ethylene-propylene-diene terpolymer; and block copolymers of styrene, e.g. styrene-butadiene-styrene, styrene-isoprene-styrene, styrene-ethylene/butylene-styrene, or styrene-ethylene/propylene-styrene.

The polymers preferably comprise graft polymers of styrene or alpha-methylstyrene, e.g. styrene onto polybutadiene, styrene onto polybutadiene-styrene copolymers or onto polybutadiene-acrylonitrile copolymers, styrene and acrylonitrile (or methacrylonitrile) onto polybutadiene; styrene, acrylonitrile, and methyl methacrylate onto polybutadiene; styrene and maleic anhydride onto polybutadiene; styrene, acrylonitrile, and maleic anhydride or maleimide onto polybutadiene; styrene and maleimide onto polybutadiene, styrene and alkyl acrylates or alkyl methacrylates onto polybutadiene, styrene and acrylonitrile on ethylene-propylene-diene terpolymers, styrene and acrylonitrile on polyalkyl acrylates or on polyalkyl methacrylates, styrene and acrylonitrile on acrylate-butadiene copolymers, and also their mixtures, e.g. those known as ABS polymers, MBS polymers, ASA polymers, or AES polymers.

The polymers preferably comprise halogen-containing polymers, e.g. polychloroprene, chlorinated rubber, chlorinated and brominated copolymer of isobutylene-isoprene (halobutyl rubber), chlorinated or chlorosulfonated polyethylene, copolymers of ethylene and of chlorinated ethylene, epichlorohydrin homo- and copolymers, in particular polymers of halogen-containing vinyl compounds, e.g. polyvinyl chloride, polyvinylidene chloride, polyvinyl fluoride, polyvinylidene fluoride; and their copolymers, such as vinyl chloride-vinylidene chloride, vinyl chloride-vinyl acetate, or vinylidene chloride-vinyl acetate.

The polymers preferably comprise polymers which derive from alpha-beta-unsaturated acids and from their derivatives, examples being polyacrylates and polymethacrylates, butyl-acrylate-impact-modified polymethyl methacrylates, polyacrylamides, polyacrylonitriles, and copolymers of the monomers mentioned with one another or with other unsaturated monomers, e.g. acrylonitrile-butadiene copolymers, acrylonitrile-alkyl acrylate copolymers, acrylonitrile-alkoxyalkyl acrylate copolymers, acrylonitrile-vinyl halide copolymers, or acrylonitrile-alkyl methacrylate-butadiene terpolymers.

The polymers preferably comprise polymers which derive from unsaturated alcohols and amines or from their acyl derivatives or acetals, examples being polyvinyl alcohol, polyvinyl acetate, polyvinyl stearate, polyvinyl benzoate, polyvinyl maleate, polyvinyl butyral, polyallyl phthalate, polyallylmelamine; and their copolymers with olefins.

The polymers preferably comprise homo- and copolymers of cyclic ethers, examples being polyalkylene glycols, polyethylene oxide, polypropylene oxide, or their copolymers with bisglycidyl ethers.

The polymers preferably comprise polyacetals, such as polyoxymethylene, and polyoxymethylenes which contain comonomers, e.g. ethylene oxide; polyacetals in which thermoplastic polyurethanes, acrylates, or MBS have been used as modifiers.

The polymers preferably comprise polyphenylene oxides and polyphenylene sulfides and their mixtures with styrene polymers or with polyamides.

The polymers preferably comprise polyurethanes which derive from, on the one hand, polyethers, polyesters, and polybutadienes having terminal hydroxy groups and, on the other hand, from aliphatic or aromatic polyisocyanates, and also comprise their precursors.

The polymers preferably comprise polyamides and copolyamides which derive from diamines and dicarboxylic acids, and/or from aminocarboxylic acids or from the corresponding lactams, examples being nylon-2,12, nylon-4 (poly (4-aminobutyric acid), ®Nylon 4, DuPont), nylon-4,6 (polytetramethyleneadipamide), poly(tetramethyleneadipic diamide), ®Nylon 4/6, DuPont), nylon-6 (polycaprolactam, poly(6-aminohexanoic acid), ®Nylon 6, DuPont, ®Akulon K122, DSM; ®Zytel 7301, DuPont; ®Durethan B 29, Bayer), nylon-6,6 (poly(N,N'-hexamethyleneadipic diamide), ®Nylon 6/6, DuPont, ®Zytel 101, DuPont; ®Durethan A30, ®Durethan AKV, ®Durethan AM, Bayer; ®Ultramid A3, BASF), nylon-6,9 (polyhexamethylenenonanediamide, ®Nylon 6/9, DuPont), nylon-6,10 (polyhexamethylenesebacamide, ®Nylon 6/10, DuPont), nylon-6,12 (polyhexamethylenedodecanediamide, ®Nylon 6/12, DuPont), nylon -6,66 (polyhexamethyleneadipamide-co-caprolactam, ®Nylon 6/66, DuPont), nylon-7 (poly(7-aminoheptanoic acid), ®Nylon 7, DuPont), nylon-7,7 (polyheptamethylenepimelamide, ®Nylon 7,7, DuPont), nylon -8 (poly(8-aminooctanoic acid), ®Nylon 8, DuPont), nylon-8,8 (polyoctamethylenesuberamide, ®Nylon 8,8, DuPont), nylon-9 (poly(9-aminononanoic acid), ®Nylon 9, DuPont), nylon-9,9 (polynonamethyleneazelamide, ®Nylon 9,9, DuPont), nylon-10 (poly (10-aminodecanoic acid), ®Nylon 10, DuPont), nylon-10,9 (polydecamethyleneazelamide, ®Nylon 10,9, DuPont), nylon-10,10 (polydecamethylenesebacamide, ®Nylon 10,10, DuPont), nylon-11 (poly(11-aminoundecanoic acid), ®Nylon 11, DuPont), nylon-12 (polylaurolactam, ®Nylon 12, DuPont, ®Grillamid L20, Ems Chemie), aromatic polyamides derived from m-xylene, diamine, and adipic acid; polyamides prepared from hexamethylenediamine and iso- and/or terephthalic acid (polyhexamethyleneisophthalamide, polyhexamethyleneterephthalamide), and, if appropriate, from an elastomer as modifier, e.g. poly-2,4,4-trimethylhexamethyleneterephthalamide or poly-m-phenyleneisophthalamide. Block copolymers of the abovementioned polyamides with polyolefins, with olefin copolymers, with ionomers or with chemically bonded or grafted elastomers; or with polyethers, e.g. with polyethylene glycol, polypropylene glycol, or polytetramethylene glycol. Other examples are EPDM- or ABS-modified polyamides or copolyamides; and polyamides condensed during processing ("RIM polyamide systems").

The polymers preferably comprise polyureas, polyimides, polyamideimides, polyetherimides, polyesterimides, polyhydantoins, and polybenzimidazoles.

The polymers preferably comprise polyesters which derive from dicarboxylic acids and from dialcohols, and/or from hydroxycarboxylic acids or from the corresponding lactones, examples being polyethylene terephthalate, polybutylene terephthalate (®Celanex 2500, ®Celanex 2002, Celanese; ®Ultradur, BASF), poly-1,4-dimethylolcyclohexane terephthalate, polyhydroxybenzoates, and also block polyetheresters which derive from polyethers having hydroxy end groups; and polyesters modified with polycarbonates or modified with MBS.

Other suitable polymers are polycarbonates and polyester carbonates, polysulfones, polyether sulfones, and polyether ketones, crosslinked polymers which derive on the one hand from aldehydes and on the other hand from phenols, urea, or melamine, examples being phenol-formaldehyde resins, urea-formaldehyde resins, and melamine-formaldehyde resins, drying and non-drying alkyd resins.

The polymers preferably comprise unsaturated polyester resins which derive from copolyesters of saturated and unsaturated dicarboxylic acids with polyhydric alcohols, and vinyl compounds as crosslinking agents, and their halogen-containing, flame-retardant modifications.

The polymers preferably comprise crosslinkable acrylic resins which derive from substituted acrylic esters, e.g. from epoxyacrylates, from urethane acrylates, or from polyester acrylates.

The polymers preferably comprise alkyd resins, polyester resins, and acrylate resins which have been crosslinked with melamine resins, crosslinked with urea resins, crosslinked with isocyanates, crosslinked with isocyanurates, crosslinked with polyisocyanates, or crosslinked with epoxy resins.

The polymers preferably comprise crosslinked epoxy resins which derive from aliphatic, cycloaliphatic, heterocyclic, or aromatic glycidyl compounds, e.g. products of bisphenol A diglycidyl ethers, of bisphenol F diglycidyl ethers, which are crosslinked by means of conventional hardeners, e.g. anhydrides or amines, with or without accelerators.

The polymers preferably comprise mixtures (polyblends) of the abovementioned polymers, e.g. PP/EPDM, polyamide/EPDM, or ABS, PVC/EVA, PVC/ABS, PVC/MBS, PC/ABS, PBTP/ABS, PC/ASA, PC/PBT, PVC/CPE, PVC/acrylates, POM/thermoplastic PU, PC/thermoplastic PU, POM/acrylate, POM/MBS, PPO/HIPS, PPO/PA 6.6 and copolymers, PA/HDPE, PA/PP, PA/PPO, PBT/PC/ABS or PBT/PET/PC.

Preferred forms of reinforcing materials for flame-retardant polymer molding compositions and flame-retardant polymer moldings are fibers, nonwovens, mats, textiles, strands, tapes, flexible tubes, braids, solid bodies, moldings, and hollow bodies.

Preferred materials for reinforcing materials for flame-retardant polymer molding compositions and flame-retardant polymer moldings are inorganic materials, such as E glass (aluminum boron silicate glass for general plastics reinforcement and for electrical applications), R glass and S glass (specialty glasses for high mechanical requirements and high temperature), D glass (specialty glass for increased dielectric requirements and high temperature), C glass (alkali-lime glass with increased boron addition for particular chemicals resistance), quartz glass, carbon, minerals, metal (steel, aluminum, magnesium, molybdenum, tungsten), ceramics (metal oxides).

Preferred materials for reinforcing materials for flame-retardant polymer molding compositions and flame-retardant polymer moldings are polycondensates, e.g. nylon-6 (e.g. ®Perlon), nylon-6,6 (e.g. ®Nylon), nylon-11 (e.g. ®Rilsan, ®Qiana), aromatic polyamides (poly-m-phenyleneisophthalamide (e.g. Nomex), poly-p-phenyleneterephthalamide (e.g. ®Aramid, ®Kevlar), polyethylene glycol terephthalate (e.g. ®Dacron, ®Diolen, ®Terylene, ®Trevira, ®Vestan, etc.), poly-1,4-dimethylenecyclohexane terephthalate (e.g. ®Kodel, ®Vestan X 160, etc.), polycarbonate, polyurethane elastomers (e.g. ®Dorlastan, ®Lycra, etc.).

Preferred materials for reinforcing materials for flame-retardant polymer molding compositions and flame-retardant polymer moldings are polymers, e.g. polyethylene, polypropylene, polyacrylonitrilehomopolymer, polyacrylonitrile copolymer (e.g. ®Dralon, ®Orlon), modacrylics (e.g. ®Kanekalon, ®Venel), atactic polyvinyl chloride (e.g. ®Rhovyl, ®Fibravyl), syndiotactic polyvinyl chloride (e.g. ®Leavil), polyvinyl alcohol (e.g. ®Kuralon, ®Vinylal, ®Vinylon), polytetrafluoroethylene (e.g. ®Teflon, ®Hostaflon), polystyrene (e.g. ®Polyfiber, ®Styroflex).

Preferred materials for reinforcing materials for flame-retardant polymer molding compositions and flame-retardant polymer moldings are natural and semisynthetic fibers (viscose cellulose, copper cellulose, cellulose acetate, cellulose triacetate, flax, hemp, sisal, jute, ramie, cotton).

Preferred dimensions for short glass fibers are lengths of from 0.01 to 10 mm and diameters of from 0.005 to 0.015 mm.

The addition of glass fibers to polyamides within the inventive concentration ranges leads to a marked rise in strength, stiffness, softening point, abrasion resistance, and dimensional stability.

An inventive process for preparation of flame-retardant polymer molding compositions consists in mixing, in a mixer, the flame retardant compositions and/or diorganylphosphinic salts with the polymer pellets and optionally additives, and homogenizing them in an inventive compounding assembly under inventive conditions in the polymer melt. The homogenized strand of molding composition is drawn off, cooled in a waterbath, and then pelletized.

In another embodiment, the flame retardant compositions and/or diorganylphosphinic salts, and/or the additives are fed to the stream of polymer in an extruder by way of a side-feed, and are homogenized.

Suitable compounding assemblies are single-screw extruders, for example from Berstorff GmbH, Hanover, and/or from Leistritz, Nuremberg.

Suitable compounding assemblies are multisection-screw extruders with three-section screws and/or with short-compression-section screws.

Suitable compounding assemblies are co-kneaders, e.g. from Coperion Buss Compounding Systems, Prafteln, Switzerland, e.g. MDK/E46-11D, and/or laboratory kneaders (MDK 46 from Buss, Switzerland, with L=11D).

Suitable compounding assemblies are twin-screw extruders, e.g. from Coperion Werner & Pfleiderer GmbH & Co. KG, Stuttgart (ZSK 25, ZSK30, ZSK 40, ZSK 58, ZSK MEGAcompounder 40, 50, 58, 70, 92, 119, 177, 250, 320, 350, 380), and/or from Berstorff GmbH, Hanover, and/or from Leistritz Extrusionstechnik GmbH, Nuremberg.

Suitable compounding assemblies are ring extruders, e.g. from 3+Extruder GmbH, Laufen, with a ring of from three to twelve small screws which rotate around a static core, and/or planetary-gear extruders, e.g. from Entex, Bochum, and/or vented extruders, and/or cascade extruders, and/or Maillefer screws.

Suitable compounding assemblies are compounders with a counter-rotating twin screw (e.g. Compex 37 or Compex 70 from Krauss-Maffei Berstorff.

Effective inventive screw lengths for single-screw extruders are from 20 to 40D.

Effective screw lengths (L) for multisection-screw extruders are 25D, with feed section (L=10D), transition section (L=6D), metering section (L=9D), effective screw lengths for twin-screw extruders are from 8 to 48D.

The flame-retardant polymer molding composition is preferably in pellet form (compounded material). The pellets preferably have the shape of a cylinder with a circular, elliptical, or irregular base, or of a sphere, cushion, cube, parallelpiped, or prism.

The length:diameter ratio of the pellets is from 1:50 to 50:1, preferably from 1:5 to 5:1.

The diameter of the pellets is preferably from 0.5 to 15 mm, particularly preferably from 2 to 3 mm, and their length is preferably from 0.5 to 15 mm, particularly preferably from 2 to 5 mm.

The pellets obtained are dried, by way of example, for 10 h at 90° C. in an oven with air circulation.

The residual moisture level of the inventive flame-retardant polymer molding compositions is from 0.01 to 10% by weight, preferably from 0.1 to 1% by weight. Residual moisture levels above the preferred ranges of the invention increase the amount of polymer degradation.

For polybutylene terephthalate molding compositions, the invention prefers SV values of from 750 to 1400, particularly from 950 to 1300, and particularly from 1000 to 1200.

The volume flow index (melt flow index, MFI, MVR) can also be utilized to assess compatibility. A marked rise in MVR value indicates polymer degradation.

For inventive glass-fiber-reinforced flame-retardant polymer molding compositions based on nylon-6,6, the value is from 2 to 200 $cm^3$/min (275° C., 5 kg).

According to the invention, the inventive flame-retardant polymer molding compositions are then used to produce flame-retardant polymer moldings.

Finally, the invention also provides polymer moldings, polymer films, polymer filaments, and polymer fibers comprising the inventive diorganylphosphinic salts and/or the inventive flame retardant compositions, and/or the inventive flame-retardant polymer molding compositions.

The invention prefers the use of the inventive diorganylphosphinic salts or of the inventive flame retardant compositions in flame-retardant polymer moldings, in flame-retardant polymer films, in flame-retardant polymer filaments, or in flame-retardant polymer fibers.

The invention prefers the use of the inventive flame-retardant polymer molding compositions in flame-retardant polymer moldings, in flame-retardant polymer films, in flame-retardant polymer filaments, or in flame-retardant polymer fibers.

The inventive flame-retardant polymer molding compositions are suitable for production of fibers, films, or moldings, in particular for applications in the electrical and electronics sector.

The invention prefers the use of the inventive flame-retardant polymer moldings as lamp parts, such as lamp sockets and lamp holders, plugs and multipoint connectors, coil formers, casings for capacitors or connectors, and circuit-breakers, relay housings, and reflectors.

The polymer of the polymer moldings, of the polymer films, of the polymer filaments, or of the polymer fibers preferably comprises a thermoplastic or thermoset polymer.

The polymer moldings, polymer films, polymer filaments, or polymer fibers preferably comprise
from 1 to 50% by weight of inventive diorganylphosphinic salts
from 1 to 99% by weight of polymer or a mixture of these
from 0 to 60% by weight of additives
from 0 to 60% by weight of filler or of reinforcing materials.

The polymer moldings, polymer films, polymer filaments, or polymer fibers preferably comprise
from 1 to 50% by weight of inventive diorganylphosphinic salts
from 1 to 99% by weight of polymer or a mixture of these
from 0.1 to 60% by weight of additives
from 0.1 to 60% by weight of filler or of reinforcing materials.

The polymer moldings, polymer films, polymer filaments, or polymer fibers preferably comprise
from 5 to 30% by weight of inventive diorganylphosphinic salts
from 5 to 90% by weight of polymer or a mixture of these
from 5 to 40% by weight of additives
from 5 to 40% by weight of filler or of reinforcing materials.

The polymer moldings, polymer films, polymer filaments, or polymer fibers preferably comprise
from 1 to 70% by weight of inventive flame retardant compositions
from 1 to 99% by weight of polymer or a mixture of these
from 0.1 to 60% by weight of additives
from 0.1 to 60% by weight of filler or of reinforcing materials.

The polymer moldings, polymer films, polymer filaments, or polymer fibers preferably comprise
from 1 to 99% by weight of inventive flame-retardant plastics molding compositions
from 1 to 99% by weight of polymer or a mixture of these
from 0.1 to 60% by weight of additives
from 0.1 to 60% by weight of filler or of reinforcing materials.

Surprisingly, it has been found that the mechanical properties of polymer moldings based on the inventive diorganylphosphinic salts, flame retardants, or flame-retardant molding compositions are considerably better than those of the prior art.

The modulus of elasticity of polymer moldings which are based on the inventive diorganylphosphinic salts, flame retardants, or flame-retardant molding compositions and polybutylene terephthalate is preferably from 10 000 to 12 000 $N/mm^2$.

The modulus of elasticity of polymer moldings which are based on the inventive diorganylphosphinic salts, flame retardants, or flame-retardant molding compositions and nylon-6,6 is preferably from 10 000 to 12 000 $N/mm^2$.

The modulus of elasticity of polymer moldings which are based on the inventive diorganylphosphinic salts, flame retardants, or flame-retardant molding compositions and nylon-6 is preferably from 10 000 to 12 000 $N/mm^2$.

Preferred process for production of flame-retardant polymer moldings is injection molding and compression molding, foam injection molding, internal-gas-pressure injection molding, blowmolding, film casting, calendering, lamination, coating, spinning, etc.

Preferred additives for flame-retardant polymer molding compositions and flame-retardant polymer moldings are antioxidants (e.g. alkylated monophenols, alkylthiomethylphenols, hydroquinones, and alkylated hydroquinones, hydroxylated thiodiphenyl ethers, alkylidenebisphenols, O-, N-, and S-benzyl compounds, hydroxybenzylated malonates, hydroxybenzyl aromatics, triazine compounds, benzyl phosphonates, acylaminophenols, esters of beta-(3,5-di-tert-butyl-4-hydroxyphenyl)propionic acid with mono- or polyhydric alcohols, esters of beta-(5-tert-butyl-4-hydroxy-3-methylphenyl)propionic acid with mono- or polyhydric alcohols, esters of beta-(3,5-dicyclohexyl-4-hydroxyphenyl) propionic acid with mono- or polyhydric alcohols, esters of 3,5-di-tert-butyl-4-hydroxyphenylacetic acid with mono- or polyhydric alcohols, amides of beta-(3,5-di-tert-butyl-4-hydroxyphenyl)propionic acid, ascorbic acid (vitamin C), aminic antioxidants.

Preferred additives for flame-retardant polymer molding compositions and flame-retardant polymer moldings are UV absorbers, and light stabilizers, 2-(2'-hydroxyphenyl)benzotriazoles, 2-hydroxybenzophenones, esters of unsubstituted or substituted benzoic acids, acrylates; nickel complexes of 2,2'-thiobis[4-(1,1,3,3-tetramethylbutyl)phenol], nickel salts of monoalkyl esters of 4-hydroxy-3,5-di-tert-butylbenzylphosphonic acid, nickel complexes of ketoximes, nickel complexes of 1-phenyl-4-lauroyl-5-hydroxypyrazole, where appropriate with additional ligands; sterically hindered amines, oxalamides, 2-(2-hydroxyphenyl)-1,3,5-triazines.

Preferred additives for flame-retardant polymer molding compositions and flame-retardant polymer moldings are lubricants, colorants, antistatic agents, nucleating agents, e.g. inorganic substances, e.g. talc, metal oxides, such as titanium dioxide or magnesium oxide, phosphates, carbonates, or sulfates of, preferably, alkaline earth metals; organic compounds, such as mono- or polycarboxylic acids, or else their salts, e.g. 4-tert-butylbenzoic acid, adipic acid, diphenylacetic acid, sodium succinate, or sodium benzoate; polymeric compounds, e.g. ionic copolymers ("ionomers").

Preferred additives for flame-retardant polymer molding compositions and flame-retardant polymer moldings are fillers (e.g. chalk and calcium carbonate, silicates, phyllosilicates, clay minerals, e.g. bentonite, montmorillonite, hectorite, saponite, precipitated/fumed/crystalline/amorphous silicas, glass beads, talc, kaolin, mica, barium sulfate, metal oxides, and metal hydroxides, oxides and/or hydroxides of the elements of the second and third main group of the Periodic Table of the Elements (preferably aluminum and magnesium), carbon black, graphite, wood flour, and flours or fibers derived from other natural products, or synthetic fibers). EP-A-0 584 567 gives examples of the additives which can be used.

An inventive flame-retardant coating comprises at least from 1 to 50% of inventive flame retardant composition from 0 to 60% of ammonium polyphosphate.

EXPERIMENTAL SECTION

Use of Microtrac granulometer to determine grain size distribution Particle size in aqueous dispersion is determined with the aid of a Microtrac ASVR/FRA granulometer from Leeds and Northrup. The reflection or scattering of the light beam is measured on passage through the dispersion. For this, 400 ml of ethanol are pumped through the laser measurement cell. The solid specimen (e.g. 70 mg) is metered in automatically and the particle size distribution is determined after 10 min. The evaluation unit of the device calculates the d50 value and the d90 value.

Determination of Total Sulfate Content

A specimen of the inventive diorganylphosphinic salt is dissolved in a solvent (preferably water, sodium hydroxide solution, or hydrochloric acid), and the sulfate is quantified by the usual methods (ion chromatography being preferred).

Determination of Soluble Sulfate Content 90 g of a 2% strength isopropanol solution are weighed into a 250 ml glass beaker and heated to 90° C. in a temperature-controlled bath, and stirred at 900 rpm, using a dissolver disk. 10 g of diorganylphosphinic salt are then added. The suspension is stirred for 5 min at 900 rpm and at 90° C. The solid is filtered off, using a suction funnel (filter: black-ribbon, 9 cm diameter), and the filtercake is then washed with 20 g of deionized water heated to about 90° C. The filtrate is made up to 100 g with deionized water. The solution is analyzed for sulfate content by means of ion chromatography. Soluble sulfate content is calculated as follows: sulfate content (specimen) [mg/kg]=sulfate content (in filtrate) [mg/kg]*final volume [mg]/input weight of diorganylphosphinic salt [mg]

Determination of SV Value (Specific Viscosity)

0.5 g of the polymer specimen (e.g. PBT) are weighed with 50 ml of dichloroacetic acid (S) into a 250 ml Erlenmeyer flask with ground-glass stopper. The specimen is dissolved over a period of 16 h at 25° C., with stirring. The solution is filtered through a G1 glass frit. 20 ml of the solution are charged to the capillary, suspended in the (Ubbelohde) capillary viscometer and temperature-dissolved at 25° C. The SV value is calculated from the formula: SV value=100*[flow time (specimen solution)/flow time (S)−1].

For polyethylene terephthalate and polybutylene terephthalate, a mixture of phenol and 1,2-dichlorobenzene (1:1, w/w) or m-cresol can also be used instead of dichloroacetic acid. For polyamide, sulfuric acid, formic acid, or m-cresol can be used.

Production, processing, and testing of flame-retardant compounded materials and a plastics molding The flame retardant components are mixed with the polymer pellets and optionally with additives and incorporated in a twin-screw extruder (Leistritz LSM 30/34) at temperatures of from 230 to 260° C. (glass-fiber-reinforced PBT) or from 260 to 280° C. (glass-fiber-reinforced PA 66). The homogenized polymer extrudate was drawn off, cooled in a water-bath, and then pelletized.

After sufficient drying, the molding compositions were processed in an injection molding machine (Aarburg Allrounder) at melt temperatures of from 240 to 270° C. (glass-fiber-reinforced PBT) or from 260 to 290° C. (glass-fiber-reinforced PA 66) to give test specimens.

EXAMPLE 1

Comparison, Untreated Polymer 70 g of predried ®Celanex 2500 (PBT) are mixed in a laboratory kneader at 40 rpm for a period of 6 min at 240° C. After cooling, the SV value of a specimen of the composition is determined as 1386.

EXAMPLE 2

Comparison 56 g of predried ®Celanex 2500 (PBT) and 14 g of diorganylphosphinic salt of DE19851618 (1997DE128), example 2 (acetate content 8800 ppm) are mixed in a laboratory kneader at 40 rpm for a period of 6 min at 240° C. After cooling, the SV value of a specimen of the composition is determined as 578. This value indicates insufficient compatibility of the diorganylphosphinic salt with the polymer.

EXAMPLE 3

Comparison 56 g of predried ®Celanex 2500 (PBT) and 14 g of diorganylphosphinic salt of DE19851618 (1997DE128), example 4 (acetate content 4500 ppm) are mixed in a laboratory kneader at 40 rpm for a period of 6 min at 240° C. After cooling, the SV value of a specimen of the composition is determined as 589. This value indicates insufficient compatibility of the diorganylphosphinic salt with the polymer.

EXAMPLE 4

56 g of predried ®Celanex 2500 (PBT) and 14 g of diorganylphosphinic salt (total acetate content 3000 ppm, soluble acetate content 1680 ppm) are mixed in a laboratory kneader at 40 rpm for a period of 6 min at 240° C. After cooling, the SV value of a specimen of the composition is determined as 673.

EXAMPLE 5

56 g of predried ®Celanex 2500 (PBT) and 14 g of diorganylphosphinic salt (total acetate content 2740 ppm, soluble acetate content 1090 ppm) are mixed in a laboratory kneader at 40 rpm for a period of 6 min at 240° C. After cooling, the SV value of a specimen of the composition is determined as 864.

EXAMPLE 6

56 g of predried ®Celanex 2500 (PBT) and 14 g of diorganylphosphinic salt (total acetate content 1990 ppm, soluble acetate content 716 ppm) are mixed in a laboratory kneader at 40 rpm for a period of 6 min at 240° C. After cooling, the SV value of a specimen of the composition is determined as 943.

EXAMPLE 7

56 g of predried ®Celanex 2500 (PBT) and 14 g of diorganylphosphinic salt (total acetate content 330 ppm, soluble acetate content 49 ppm) are mixed in a laboratory kneader at 40 rpm for a period of 6 min at 240° C. After cooling, the SV value of a specimen of the composition is determined as 1099.

EXAMPLE 8

56 g of predried ®Celanex 2500 (PBT) and 14 g of diorganylphosphinic salt (total acetate content 140 ppm, soluble acetate content 10 ppm) are mixed in a laboratory kneader at 40 rpm for a period of 6 min at 240° C. After cooling, the SV value of a specimen of the composition is determined as 1180.

EXAMPLE 9

Comparison 56 g of predried ®Celanex 2500 (PBT) and 14 g of diorganylphosphinic salt (total chloride content 1950 ppm, soluble chloride content 1073 ppm) are mixed in a laboratory kneader at 40 rpm for a period of 6 min at 240° C. After cooling, the SV value of a specimen of the composition is determined as 608. This value indicates insufficient compatibility of the diorganylphosphinic salt with the polymer.

EXAMPLE 10

56 g of predried ®Celanex 2500 (PBT) and 14 g of diorganylphosphinic salt (total chloride content 1677 ppm, soluble chloride content 805 ppm) are mixed in a laboratory kneader at 40 rpm for a period of 6 min at 240° C. After cooling, the SV value of a specimen of the composition is determined as 805.

EXAMPLE 11

56 g of predried ®Celanex 2500 (PBT) and 14 g of diorganylphosphinic salt (total chloride content 1257 ppm, soluble chloride content 357 ppm) are mixed in a laboratory kneader at 40 rpm for a period of 6 min at 240° C. After cooling, the SV value of a specimen of the composition is determined as 948.

EXAMPLE 12

56 g of predried ®Celanex 2500 (PBT) and 14 g of diorganylphosphinic salt (total chloride content 584 ppm, soluble chloride content 70 ppm) are mixed in a laboratory kneader at 40 rpm for a period of 6 min at 240° C. After cooling, the SV value of a specimen of the composition is determined as 1121.

EXAMPLE 13

56 g of predried ®Celanex 2500 (PBT) and 14 g of diorganylphosphinic salt (total chloride content 280 ppm, soluble chloride content 18 ppm) are mixed in a laboratory kneader at 40 rpm for a period of 6 min at 240° C. After cooling, the SV value of a specimen of the composition is determined as 1242.

EXAMPLE 14

Comparison 56 g of predried ®Celanex 2500 (PBT) and 14 g of diorganylphosphinic salt (total nitrate content 2204 ppm, soluble nitrate content 1411 ppm) are mixed in a laboratory kneader at 40 rpm for a period of 6 min at 240° C. After cooling, the SV value of a specimen of the composition is determined as 654. This value indicates insufficient compatibility of the diorganylphosphinic salt with the polymer.

EXAMPLE 15

56 g of predried ®Celanex 2500 (PBT) and 14 g of diorganylphosphinic salt (total nitrate content 2100 ppm, soluble nitrate content 1134 ppm) are mixed in a laboratory kneader at 40 rpm for a period of 6 min at 240° C. After cooling, the SV value of a specimen of the composition is determined as 781.

EXAMPLE 16

56 g of predried ®Celanex 2500 (PBT) and 14 g of diorganylphosphinic salt (total nitrate content 820 ppm, soluble nitrate content 295 ppm) are mixed in a laboratory kneader at 40 rpm for a period of 6 min at 240° C. After cooling, the SV value of a specimen of the composition is determined as 1029.

EXAMPLE 17

56 g of predried ®Celanex 2500 (PBT) and 14 g of diorganylphosphinic salt (total nitrate content 177 ppm, soluble nitrate content 21 ppm) are mixed in a laboratory kneader at 40 rpm for a period of 6 min at 240° C. After cooling, the SV value of a specimen of the composition is determined as 1207.

EXAMPLE 18

56 g of predried ®Celanex 2500 (PBT) and 14 g of diorganylphosphinic salt (total nitrate content 164 ppm, soluble nitrate content 13 ppm) are mixed in a laboratory kneader at 40 rpm for a period of 6 min at 240° C. After cooling, the SV value of a specimen of the composition is determined as 1252.

EXAMPLE 19

Comparison 56 g of predried ®Celanex 2500 (PBT) and 14 g of diorganylphosphinic salt (total phosphite content 9425 ppm, soluble phosphite content 3582 ppm) are mixed in a laboratory kneader at 40 rpm for a period of 6 min at 240° C. After cooling, the SV value of a specimen of the composition is determined as 571. This value indicates insufficient compatibility of the diorganylphosphinic salt with the polymer.

EXAMPLE 20

56 g of predried ®Celanex 2500 (PBT) and 14 g of diorganylphosphinic salt (total phosphite content 8125 ppm, soluble phosphite content 3088 ppm) are mixed in a laboratory kneader at 40 rpm for a period of 6 min at 240° C. After cooling, the SV value of a specimen of the composition is determined as 753.

EXAMPLE 21

56 g of predried ®Celanex 2500 (PBT) and 14 g of diorganylphosphinic salt (total phosphite content 6500 ppm, soluble phosphite content 1820 ppm) are mixed in a laboratory kneader at 40 rpm for a period of 6 min at 240° C. After cooling, the SV value of a specimen of the composition is determined as 878.

EXAMPLE 22

56 g of predried ®Celanex 2500 (PBT) and 14 g of diorganylphosphinic salt (total phosphite content 1138 ppm, soluble phosphite content 159 ppm) are mixed in a laboratory kneader at 40 rpm for a period of 6 min at 240° C. After cooling, the SV value of a specimen of the composition is determined as 1167.

EXAMPLE 23

56 g of predried ®Celanex 2500 (PBT) and 14 g of diorganylphosphinic salt (total phosphite content 650 ppm, soluble phosphite content 59 ppm) are mixed in a laboratory kneader at 40 rpm for a period of 6 min at 240° C. After cooling, the SV value of a specimen of the composition is determined as 1250.

EXAMPLE 24

Comparison 56 g of predried ®Celanex 2500 (PBT) and 14 g of diorganylphosphinic salt (total sulfate content 5070 ppm, soluble sulfate content 1300 ppm) are mixed in a laboratory kneader at 40 rpm for a period of 6 min at 240° C. After the SV value of a specimen of the composition is determined as 582. This value indicates insufficient compatibility of the diorganylphosphinic salt with the polymer.

EXAMPLE 25

56 g of predried ®Celanex 2500 (PBT) and 14 g of diorganylphosphinic salt (total sulfate content 3900 ppm, soluble sulfate content 866 ppm) are mixed in a laboratory kneader at 40 rpm for a period of 6 min at 240° C. After cooling, the SV value of a specimen of the composition is determined as 785.

EXAMPLE 26

56 g of predried ®Celanex 2500 (PBT) and 14 g of diorganylphosphinic salt (total sulfate content 2510 ppm, soluble sulfate content 42 ppm) are mixed in a laboratory kneader at 40 rpm for a period of 6 min at 240° C. After cooling, the SV value of a specimen of the composition is determined as 1012.

EXAMPLE 27

56 g of predried ®Celanex 2500 (PBT) and 14 g of diorganylphosphinic salt (total sulfate content 640 ppm, soluble sulfate content 521 ppm) are mixed in a laboratory kneader at 40 rpm for a period of 6 min at 240° C. After cooling, the SV value of a specimen of the composition is determined as 1158.

EXAMPLE 28

56 g of predried ®Celanex 2500 (PBT) and 14 g of diorganylphosphinic salt (total sulfate content 200 ppm, soluble sulfate content 21 ppm) are mixed in a laboratory kneader at 40 rpm for a period of 6 min at 240° C. After cooling, the SV value of a specimen of the composition is determined as 1196.

EXAMPLE 29

Comparison

In accordance with the general specification, a mixture of 50% by weight of polybutylene terephthalate, 15% by weight of phosphinic salt from example 2, 5% by weight of melamine cyanurate and 30% by weight of glass fibers are compounded in a twin-screw extruder at from 230 to 260° C. to give a polymer molding composition. After drying, the molding compositions are processed in an injection molding machine at from 240 to 270° C. to give a polymer molding, and a modulus of elasticity of 9150 N/mm$^2$ is measured. This modulus of elasticity of a polymer molding based on a phosphinic salt of the prior art is poorer than that of example 35, in which an inventive phosphinic salt was used.

EXAMPLE 30

Comparison

In accordance with the general specification, a mixture of 50% by weight of polybutylene terephthalate, 15% by weight of phosphinic salt from example 3, 5% by weight of melamine cyanurate and 30% by weight of glass fibers are compounded in a twin-screw extruder at from 230 to 260° C. to give a polymer molding composition. After drying, the molding compositions are processed in an injection molding machine at from 240 to 270° C. to give a polymer molding, and a modulus of elasticity of 9573 N/mm$^2$ is measured. This modulus of elasticity of a polymer molding based on a phosphinic salt of the prior art is poorer than that of example 35, in which an inventive phosphinic salt was used.

EXAMPLE 31

In accordance with the general specification, a mixture of 50% by weight of polybutylene terephthalate, 2% by weight of phosphinic salt from example 7, 18% by weight of melamine cyanurate and 30% by weight of glass fibers are compounded in a twin-screw extruder at from 230 to 260° C. to give a polymer molding composition. After drying, the molding compositions are processed in an injection molding machine at from 240 to 270° C. to give a polymer molding, and a modulus of elasticity of 12 100 N/mm$^2$ is measured. This modulus of elasticity of a polymer molding based on an inventive phosphinic salt is better than those of examples 29 and 30, in which phosphinic salts of the prior art were used. A V-1 UL 94 classification was also determined.

EXAMPLE 32

In accordance with the general specification, a mixture of 50% by weight of polybutylene terephthalate, 5% by weight of phosphinic salt from example 12, 15% by weight of melamine cyanurate and 30% by weight of glass fibers is compounded in a twin-screw extruder at from 230 to 260° C. to give a polymer molding composition. After drying, the molding compositions are processed in an injection molding machine at from 240 to 270° C. to give a polymer molding, and a modulus of elasticity of 10 480 N/mm$^2$ is measured. This modulus of elasticity of a polymer molding based on an inventive phosphinic salt is better than those of examples 29 and 30, in which phosphinic salts of the prior art were used. A V-0 UL 94 classification was also determined. Because the UL 94 classification is better, the constitution of the flame retardant formulation underlying this example and comprising phosphinic salt and melamine cyanurate, the constitution of the polymer molding composition underlying this example and comprising polybutylene terephthalate and flame retardant formulation (comprising phosphinic salt and melamine cyanurate) and the polymer molding constitution underlying this example and comprising polymer molding compositions and additives are preferred over those which give V-1 and V-2 classifications.

EXAMPLE 33

In accordance with the general specification, a mixture of 50% by weight of polybutylene terephthalate, 6.7% by weight of phosphinic salt from example 22, 13.3% by weight of melamine cyanurate and 30% by weight of glass fibers is compounded in a twin-screw extruder at from 230 to 260° C. to give a polymer molding composition. After drying, the molding compositions are processed in an injection molding machine at from 240 to 270° C. to give a polymer molding, and a modulus of elasticity of 10 130 N/mm$^2$ is measured. This modulus of elasticity of a polymer molding based on an inventive phosphinic salt is better than those of examples 29 and 30, in which phosphinic salts of the prior art were used. A V-0 UL 94 classification was also determined. Because the UL 94 classification is better, the constitution of the flame retardant formulation underlying this example and comprising phosphinic salt and melamine cyanurate, the constitution of the polymer molding composition underlying this example and comprising polybutylene terephthalate and flame retardant formulation (comprising phosphinic salt and melamine cyanurate) and the polymer molding constitution underlying this example and comprising polymer molding compositions and additives are preferred over those which give V-1 and V-2 classifications.

EXAMPLE 34

In accordance with the general specification, a mixture of 50% by weight of polybutylene terephthalate, 13.3% by weight of phosphinic salt from example 27, 6.7% by weight of melamine cyanurate and 30% by weight of glass fibers is compounded in a twin-screw extruder at from 230 to 260° C. to give a polymer molding composition. After drying, the molding compositions are processed in an injection molding machine at from 240 to 270° C. to give a polymer molding, and a modulus of elasticity of 10 350 N/mm$^2$ is measured. This modulus of elasticity of a polymer molding based on an inventive phosphinic salt is better than those of examples 29 and 30, in which phosphinic salts of the prior art were used. A V-0 UL 94 classification was also determined. Because the UL 94 classification is better, the constitution of the flame retardant formulation underlying this example and comprising phosphinic salt and melamine cyanurate, the constitution of the polymer molding composition underlying this example and comprising polybutylene terephthalate and flame retardant formulation (comprising phosphinic salt and melamine cyanurate) and the polymer molding constitution underlying this example and comprising polymer molding compositions and additives are preferred over those which give V-1 and V-2 classifications.

EXAMPLE 35

In accordance with the general specification, a mixture of 50% by weight of polybutylene terephthalate, 15% by weight of phosphinic salt from example 28, 5% by weight of melamine cyanurate and 30% by weight of glass fibers is compounded in a twin-screw extruder at from 230 to 260° C. to give a polymer molding composition. After drying, the molding compositions are processed in an injection molding machine at from 240 to 270° C. to give a polymer molding, and a modulus of elasticity of 10 510 N/mm$^2$ is measured. This modulus of elasticity of a polymer molding based on an inventive phosphinic salt is better than those of examples 29 and 30, in which phosphinic salts of the prior art were used. A V-0 UL 94 classification was also determined. Because the UL 94 classification is better, the constitution of the flame retardant formulation underlying this example and comprising phosphinic salt and melamine cyanurate, the constitution of the polymer molding composition underlying this example and comprising polybutylene terephthalate and flame retardant formulation (comprising phosphinic salt and melamine cyanurate) and the polymer molding constitution underlying this example and comprising polymer molding compositions and additives are preferred over those which give V-1 and V-2 classifications.

EXAMPLE 36

Following the general specification, a mixture of 50% by weight of polybutylene terephthalate, 20% by weight of phosphinic salt from example 15, and 30% by weight of glass fibers were compounded in a twin-screw extruder at from 230 to 260° C. to give a polymer molding composition. After drying, the molding compositions are processed in an injection molding machine at from 240 to 270° C. to give a polymer molding and a UL 94 classification of V-0 is determined.

EXAMPLE 37

Following the general specification, a mixture of 50% by weight of polybutylene terephthalate, 13.3% by weight of phosphinic salt from example 27, 6.7% by weight of melamine polyphosphate, and 30% by weight of glass fibers is compounded in a twin-screw extruder at from 230 to 260° C. to give a polymer molding composition. After drying, the molding compositions are processed in an injection molding machine at from 240 to 270° C. to give a polymer molding, and a UL 94 classification of V-0 is determined. Because the UL 94 classification is better, the constitution of the flame retardant formulation underlying this example and comprising phosphinic salt and melamine polyphosphate, the constitution of the polymer molding composition underlying this example and comprising polybutylene terephthalate and flame retardant formulation (comprising phosphinic salt and melamine polyphosphate) and the polymer molding constitution underlying this example and comprising polymer molding compositions and additives are preferred over those which give V-1 and V-2 classifications.

EXAMPLE 38

Following the general specification, a mixture of 50% by weight of polybutylene terephthalate, 6.7% by weight of phosphinic salt from example 23,13.3% by weight of melamine polyphosphate, and 30% by weight of glass fibers is compounded in a twin-screw extruder at from 230 to 260° C. to give a polymer molding composition. After drying, the molding compositions are processed in an injection molding machine at from 240 to 270° C. to give a polymer molding, and a UL 94 classification of V-0 is determined. Because the UL 94 classification is better, the constitution of the flame retardant formulation underlying this example and comprising phosphinic salt and melamine polyphosphate, the constitution of the polymer molding composition underlying this example and comprising polybutylene terephthalate and flame retardant formulation (comprising phosphinic salt and melamine polyphosphate) and the polymer molding constitution underlying this example and comprising polymer molding compositions and additives are preferred over those which give V-1 and V-2 classifications.

EXAMPLE 39

Following the general specification, a mixture of 50% by weight of polybutylene terephthalate, 2% by weight of phosphinic salt from example 8, and 18% by weight of melamine polyphosphate and 30% by weight of glass fibers were compounded in a twin-screw extruder at from 230 to 260° C. to give a polymer molding composition. After drying, the molding compositions are processed in an injection molding machine at from 240 to 270° C. to give a polymer molding and a UL 94 classification of V-1 is determined.

EXAMPLE 39a

Comparison

Following the general specification, a mixture of 50% by weight of nylon-6,6, 13.3% by weight of phosphinic salt from example 2, 6.7% by weight of melamine polyphosphate and 30% by weight of glass fibers is compounded in a twin-screw extruder at from 230 to 260° C. to give a polymer molding composition. After drying, the molding compositions are processed in an injection molding machine at from 240 to 270° C. to give a polymer molding, and a modulus of elasticity of 9000 N/mm$^2$ is measured. This modulus of elasticity of a polymer molding based on a phosphinic salt of the prior art is poorer than that of example 40, in which an inventive phosphinic salt was used. A UL 94 classification of V-0 was also determined.

EXAMPLE 40

Following the general specification, a mixture of 50% by weight of nylon-6,6, 13.3% by weight of phosphinic salt from example 28, 6.7% by weight of melamine polyphosphate and 30% by weight of glass fibers is compounded in a twin-screw extruder at from 230 to 260° C. to give a polymer molding composition. After drying, the molding compositions are processed in an injection molding machine at from 240 to 270° C. to give a polymer molding, and a modulus of elasticity of 11 500 N/mm$^2$ is measured. This modulus of elasticity of a polymer molding based on an inventive phosphinic salt is better than that of example 39a, in which a phosphinic salt of the prior art was used. A UL 94 classification of V-0 was also determined. Because the UL 94 classification is better, the constitution of the flame retardant formulation underlying this example and comprising phosphinic salt and melamine polyphosphate, the constitution of the polymer molding composition underlying this example and comprising polyamide and flame retardant formulation (comprising phosphinic salt and melamine polyphosphate) and the polymer molding constitution underlying this example and comprising polymer molding compositions and additives are preferred over those which give V-1 and V-2 classifications.

EXAMPLE 41

Following the general specification, a mixture of 50% by weight of nylon-6,6, 6.7% by weight of phosphinic salt from example 13, 13.3% by weight of melamine polyphosphate and 30% by weight of glass fibers is compounded in a twin-screw extruder at from 230 to 260° C. to give a polymer molding composition. After drying, the molding compositions are processed in an injection molding machine at from 240 to 270° C. to give a polymer molding, and a UL 94 classification of V-0 was determined. Because the UL 94 classification is better, the constitution of the flame retardant formulation underlying this example and comprising phosphinic salt and melamine polyphosphate, the constitution of the polymer molding composition underlying this example and comprising polyamide and flame retardant formulation (comprising phosphinic salt and melamine polyphosphate) and the polymer molding constitution underlying this example and comprising polymer molding compositions and additives are preferred over those which give V-1 and V-2 classifications.

EXAMPLE 42

Following the general specification, a mixture of 50% by weight of nylon-6,6, 2% by weight of phosphinic salt from example 23, 18% by weight of melamine polyphosphate, and 30% by weight of glass fibers is compounded in a twin-screw extruder at from 230 to 260° C. to give a polymer molding composition. After drying, the molding compositions are processed in an injection molding machine at from 240 to 270° C. to give a polymer molding, and a UL 94 classification of V-2 is determined.

EXAMPLE 43

Following the general specification, a mixture of 50% by weight of nylon-6,6, 17% by weight of phosphinic salt from example 22, 2% by weight of melamine polyphosphate, and 1% by weight of zinc borate, and 30% by weight of glass fibers is compounded in a twin-screw extruder at from 230 to 260° C. to give a polymer molding composition. After drying, the molding compositions are processed in an injection molding machine at from 240 to 270° C. to give a polymer molding, and a UL 94 classification of V-0 is determined.

EXAMPLE 44

Comparison

Following the general specification, a mixture of 50% by weight of nylon-6,6, 15% by weight of phosphinic salt from example 2, 4% by weight of melamine polyphosphate, 1% by weight of zinc borate, and 30% by weight of glass fibers is compounded in a twin-screw extruder at from 230 to 260° C. to give a polymer molding composition. After drying, the molding compositions are processed in an injection molding machine at from 240 to 270° C. to give a polymer molding, and a modulus of elasticity of 9100 N/mm$^2$ is measured. This modulus of elasticity of a polymer molding based on a phosphinic salt of the prior art is poorer than that of examples 46 and 47, in which inventive phosphinic salts were used.

EXAMPLE 45

Comparison

Following the general specification, a mixture of 50% by weight of nylon-6,6, 15% by weight of phosphinic salt from example 3, 4% by weight of melamine polyphosphate, 1% by weight of zinc borate, and 30% by weight of glass fibers is compounded in a twin-screw extruder at from 230 to 260° C. to give a polymer molding composition. After drying, the molding compositions are processed in an injection molding machine at from 240 to 270° C. to give a polymer molding, and a modulus of elasticity of 9500 N/mm$^2$ is measured. This modulus of elasticity of a polymer molding based on a phosphinic salt of the prior art is poorer than that of examples 46 and 47, in which inventive phosphinic salts were used.

EXAMPLE 46

Following the general specification, a mixture of 50% by weight of nylon-6,6, 15% by weight of phosphinic salt from example 26, 4% by weight of melamine polyphosphate, 1% by weight of zinc borate, and 30% by weight of glass fibers is compounded in a twin-screw extruder at from 230 to 260° C. to give a polymer molding composition. After drying, the molding compositions are processed in an injection molding machine at from 240 to 270° C. to give a polymer molding, and a modulus of elasticity of 11 800 N/mm$^2$ is measured. This modulus of elasticity of a polymer molding based on an inventive phosphinic salt is better than that of examples 44 and 45, in which phosphinic salts of the prior art were used. A UL 94 classification of V-0 was also determined. Because the UL 94 classification is better, the constitution of the flame retardant formulation underlying this example and comprising phosphinic salt, melamine polyphosphate, and zinc borate, the constitution of the polymer molding composition underlying this example and comprising polyamide and flame retardant formulation (comprising phosphinic salt, melamine polyphosphate, and zinc borate) and the polymer molding constitution underlying this example and comprising polymer molding compositions and additives are preferred over those which give V-1 and V-2 classifications.

EXAMPLE 47

Following the general specification, a mixture of 50% by weight of nylon-6,6, 12.7% by weight of phosphinic salt from example 27, 6.3% by weight of melamine polyphosphate, 1% by weight of zinc oxide, and 30% by weight of glass fibers is compounded in a twin-screw extruder at from 230 to 260° C. to give a polymer molding composition. After drying, the molding compositions are processed in an injection molding machine at from 240 to 270° C. to give a polymer molding, and a modulus of elasticity of 10 100 N/mm$^2$ is measured. This modulus of elasticity of a polymer molding based on an inventive phosphinic salt is better than that of examples 44 and 45, in which phosphinic salts of the prior art were used. A UL 94 classification of V-0 was also determined. Because the UL 94 classification is better, the constitution of the flame retardant formulation underlying this example and comprising phosphinic salt, melamine polyphosphate, and zinc oxide, the constitution of the polymer molding composition underlying this example and comprising polyamide and flame retardant formulation (comprising phosphinic salt, melamine polyphosphate, and zinc oxide) and the polymer molding constitution underlying this example and comprising polymer molding compositions and additives are preferred over those which give V-1 and V-2 classifications.

EXAMPLE 48

Following the general specification, a mixture of 50% by weight of nylon-6,6, 6.3% by weight of phosphinic salt from example 13, 12.7% by weight of melamine polyphosphate, 1% by weight of zinc oxide, and 30% by weight of glass fibers is compounded in a twin-screw extruder at from 230 to 260° C. to give a polymer molding composition. After drying, the molding compositions are processed in an injection molding machine at from 240 to 270° C. to give a polymer molding, and a UL 94 classification of V-0 is determined. Because the UL 94 classification is better, the constitution of the flame retardant formulation underlying this example and comprising phosphinic salt, melamine polyphosphate, and zinc oxide, the constitution of the polymer molding composition underlying this example and comprising polyamide and flame retardant formulation (comprising phosphinic salt, melamine polyphosphate, and zinc oxide) and the polymer molding constitution underlying this example and comprising polymer molding compositions and additives are preferred over those which give V-1 and V-2 classifications.

EXAMPLE 49

Following the general specification, a mixture of 50% by weight of nylon-6,6, 4% by weight of phosphinic salt from example 18, 15% by weight of melamine polyphosphate, 1% by weight of zinc hydroxystannate, and 30% by weight of glass fibers is compounded in a twin-screw extruder at from 230 to 260° C. to give a polymer molding composition. After drying, the molding compositions are processed in an injection molding machine at from 240 to 270° C. to give a polymer molding, and a UL 94 classification of V-0 is determined. Because the UL 94 classification is better, the constitution of the flame retardant formulation underlying this example and comprising phosphinic salt, melamine polyphosphate, and zinc hydroxystannate, the constitution of the polymer molding composition underlying this example and comprising polyamide and flame retardant formulation (comprising phosphinic salt, melamine polyphosphate, and zinc hydroxystannate) and the polymer molding constitution underlying this example and comprising polymer molding compositions and additives are preferred over those which give V-1 and V-2 classifications.

EXAMPLE 50

Following the general specification, a mixture of 50% by weight of nylon-6,6, 2% by weight of phosphinic salt from example 23, 17% by weight of melamine polyphosphate, 1% by weight of zinc stearate, and 30% by weight of glass fibers is compounded in a twin-screw extruder at from 230 to 260° C. to give a polymer molding composition. After drying, the molding compositions are processed in an injection molding machine at from 240 to 270° C. to give a polymer molding, and a UL 94 classification of V-2 is determined.

EXAMPLE 51

Following the general specification, a mixture of 58% by weight of nylon-6, 11.3% by weight of phosphinic salt from example 28, 5;7% by weight of melamine polyphosphate, and 25% by weight of glass fibers is compounded in a twin-screw extruder at from 230 to 260° C. to give a polymer molding composition. After drying, the molding compositions are processed in an injection molding machine at from 240 to 270° C. to give a polymer molding, and a UL 94 classification of V-0 is determined. Because the UL 94 classification is better, the constitution of the flame retardant formulation underlying this example and comprising phosphinic salt and melamine polyphosphate, the constitution of the polymer molding composition underlying this example and comprising polyamide and flame retardant formulation (comprising phosphinic salt and melamine polyphosphate) and the polymer molding constitution underlying this example and comprising polymer molding compositions and additives are preferred over those which give V-1 and V-2 classifications.

Chemicals Used
Polybutylene terephthalate: Celanex 2500, Ticona
Nylon-6,6: Ultramid A3, BASF
Nylon-6: Zytel 7301, DuPont
Melamine polyphosphate: Melapur 200/70, Ciba DSM-Melapur
Melamine cyanurate: Melapur MC, Ciba DSM-Melapur
Zinc borate: Firebrake 500, Borax
Zinc oxide: Rheinchemie
Zinc hydroxystannate: Flamtard H, Blythe
Zinc stearate: Liga 101, Greven Fett-Chemie
Glass fibers 1: Vetrotex EC 10 983, Saint-Gobain
Glass fibers 2: PPG 3540, PPG Industries, Inc

TABLE 1

| Example | Acetate | | Chloride | | Nitrate | | Phosphite | | Sulfate | | SV value |
|---|---|---|---|---|---|---|---|---|---|---|---|
| | Total ppm | Soluble ppm | Total ppm | Soluble ppm | Total ppm | Soluble ppm | Total ppm | Soluble ppm | Total ppm | Soluble ppm | |
| 1 (comp., polymer) | | | | | | | | | — | — | 1386 |
| 2 (comp.) 1997DE128 DE19851618, example | 8800 | | | | | | | | | | 578 |
| 3 (comp.) 1997DE128 DE19851618, example | 4500 | | | | | | | | | | 589 |
| 4 (comp.) | 3000 | 1680 | | | | | | | | | 673 |
| 5 | 2740 | 1090 | | | | | | | | | 864 |
| 6 | 1990 | 716 | | | | | | | | | 943 |
| 7 | 330 | 49 | | | | | | | | | 1099 |
| 8 | 140 | 10 | | | | | | | | | 1180 |
| 9 (comp.) | | | 1950 | 1073 | | | | | | | 608 |
| 10 | | | 1677 | 805 | | | | | | | 805 |
| 11 | | | 1257 | 357 | | | | | | | 948 |
| 12 | | | 584 | 70 | | | | | | | 1121 |
| 13 | | | 280 | 18 | | | | | | | 1242 |
| 14 (comp.) | | | | | 2204 | 1411 | | | | | 654 |
| 15 | | | | | 2100 | 1134 | | | | | 781 |
| 16 | | | | | 820 | 295 | | | | | 1029 |
| 17 | | | | | 177 | 21 | | | | | 1207 |
| 18 | | | | | 164 | 13 | | | | | 1252 |
| 19 (comp.) | | | | | | | 9425 | 3582 | | | 571 |
| 20 | | | | | | | 8125 | 3088 | | | 753 |
| 21 | | | | | | | 6500 | 1820 | | | 878 |
| 22 | | | | | | | 1138 | 159 | | | 1167 |
| 23 | | | | | | | 650 | 59 | | | 1250 |
| 24 (comp.) | | | | | | | | | 5070 | 1300 | 582 |
| 25 | | | | | | | | | 3900 | 866 | 785 |
| 26 | | | | | | | | | 2510 | 42 | 1012 |
| 27 | | | | | | | | | 640 | 521 | 1158 |
| 28 | | | | | | | | | 200 | 21 | 1196 |

TABLE 2

|  |  | Example |  |  |  |  |  |  |  |  |  |  |  |
|---|---|---|---|---|---|---|---|---|---|---|---|---|---|
|  |  | 29 (comp) | 30 (comp) | 31 | 32 | 33 | 34 | 35 | 36 | 37 | 38 | 39 | 39a (comp) |
| Polybutylene terephthalate | [% by wt.] | 50 | 50 | 50 | 50 | 50 | 50 | 50 | 50 | 50 | 50 | 50 | — |
| Nylon-6,6 | [% by wt.] | — | — | — | — | — | — | — | — | — | — | — | 50 |
| Nylon-6 | [% by wt.] | — | — | — | — | — | — | — | — | — | — | — | — |
| Phosphinic salt, Ex. 2 (comp) | [% by wt.] | 15 | — | — | — | — | — | — | — | — | — | — | 13.3 |
| Phosphinic salt, Ex. 3 (comp) | [% by wt.] | — | 15 | — | — | — | — | — | — | — | — | — | — |
| Phosphinic salt, Ex. 7 | [% by wt.] | — | — | 2 | — | — | — | — | — | — | — | — | — |
| Phosphinic salt, Ex. 12 | [% by wt.] | — | — | — | 5 | — | — | — | — | — | — | — | — |
| Phosphinic salt, Ex. 22 | [% by wt.] | — | — | — | — | 6.7 | — | — | — | — | — | — | — |
| Phosphinic salt, Ex. 27 | [% by wt.] | — | — | — | — | — | 13.3 | — | — | — | — | — | — |
| Phosphinic salt, Ex. 28 | [% by wt.] | — | — | — | — | — | — | 15 | — | — | — | — | — |
| Phosphinic salt, Ex. 15 | [% by wt.] | — | — | — | — | — | — | — | 20 | — | — | — | — |
| Phosphinic salt, Ex. 27 | [% by wt.] | — | — | — | — | — | — | — | — | 13.3 | — | — | — |
| Phosphinic salt, Ex. 23 | [% by wt.] | — | — | — | — | — | — | — | — | — | 6.7 | — | — |
| Phosphinic salt, Ex. 8 | [% by wt.] | — | — | — | — | — | — | — | — | — | — | 2 | — |
| Phosphinic salt, Ex. 13 | [% by wt.] | — | — | — | — | — | — | — | — | — | — | — | — |
| Phosphinic salt, Ex. 26 | [% by wt.] | — | — | — | — | — | — | — | — | — | — | — | — |
| Phosphinic salt, Ex. 18 | [% by wt.] | — | — | — | — | — | — | — | — | — | — | — | — |
| Melamine polyphosphate | [Gew-%] | — | — | — | — | — | — | — | — | 6.7 | 13.3 | 18 | 6.7 |
| Melamine cyanurate | [% by wt.] | 5 | 5 | 18 | 15 | 13.3 | 6.7 | 5 | — | — | — | — | — |
| Zinc borate | [% by wt.] | — | — | — | — | — | — | — | — | — | — | — | — |
| Zinc oxide | [% by wt.] | — | — | — | — | — | — | — | — | — | — | — | — |
| Zinc hydroxystannate | [% by wt.] | — | — | — | — | — | — | — | — | — | — | — | — |
| Zinc stearate | [% by wt.] | — | — | — | — | — | — | — | — | — | — | — | — |
| Glass fibers 1 | [% by wt.] | 30 | 30 | 30 | 30 | 30 | 30 | 30 | 30 | 30 | 30 | 30 | — |
| Glass fibers 2 | [% by wt.] | — | — | — | — | — | — | — | — | — | — | — | 30 |
| Modulus of elasticity | [N/mm2] | 9150 | 9573 | 12100 | 10480 | 10130 | 10350 | 10510 | — | — | — | — | 9000 |
| UL 94 classification | [—] | V-0 | V-0 | V-1 | V-0 | V-0 | V-0 | V-0 | V-0 | V-0 | V-0 | V-1 | V-0 |

|  |  | Example |  |  |  |  |  |  |  |  |  |  |  |
|---|---|---|---|---|---|---|---|---|---|---|---|---|---|
|  |  | 40 | 41 | 42 | 43 | 44 (comp) | 45 (comp) | 46 | 47 | 48 | 49 | 50 | 51 |
| Polybutylene terephthalate | [% by wt.] | — | — | — | — | — | — | — | — | — | — | — | — |
| Nylon-6,6 | [% by wt.] | 50 | 50 | 50 | 50 | 50 | 50 | 50 | 50 | 50 | 50 | 50 | — |
| Nylon-6 | [% by wt.] | — | — | — | — | — | — | — | — | — | — | — | 58 |
| Phosphinic salt, Ex. 2 (comp) | [% by wt.] | — | — | — | — | 15 | — | — | — | — | — | — | — |
| Phosphinic salt, Ex. 3 (comp) | [% by wt.] | — | — | — | — | — | 15 | — | — | — | — | — | — |
| Phosphinic salt, Ex. 7 | [% by wt.] | — | — | — | — | — | — | — | — | — | — | — | — |
| Phosphinic salt, Ex. 12 | [% by wt.] | — | — | — | — | — | — | — | — | — | — | — | — |
| Phosphinic salt, Ex. 22 | [% by wt.] | — | — | — | 17 | — | — | — | — | — | — | — | — |
| Phosphinic salt, Ex. 27 | [% by wt.] | — | — | — | — | — | — | — | — | — | — | — | — |
| Phosphinic salt, Ex. 28 | [% by wt.] | 13.3 | — | — | — | — | — | — | — | — | — | — | 11.3 |
| Phosphinic salt, Ex. 15 | [% by wt.] | — | — | — | — | — | — | — | — | — | — | — | — |
| Phosphinic salt, Ex. 27 | [% by wt.] | — | — | — | — | — | — | — | 12.7 | — | — | — | — |
| Phosphinic salt, Ex. 23 | [% by wt.] | — | — | 2 | — | — | — | — | — | — | — | 2 | — |
| Phosphinic salt, Ex. 8 | [% by wt.] | — | — | — | — | — | — | — | — | — | — | — | — |
| Phosphinic salt, Ex. 13 | [% by wt.] | — | 6.7 | — | — | — | — | — | — | 6.3 | — | — | — |
| Phosphinic salt, Ex. 26 | [% by wt.] | — | — | — | — | — | — | 15 | — | — | — | — | — |
| Phosphinic salt, Ex. 18 | [% by wt.] | — | — | — | — | — | — | — | — | — | 4 | — | — |
| Melamine polyphosphate | [Gew-%] | 6.7 | 13.3 | 18 | 2 | 4 | 4 | 4 | 6.3 | 12.7 | 15 | 17 | 5.7 |
| Melamine cyanurate | [% by wt.] | — | — | — | — | — | — | — | — | — | — | — | — |
| Zinc borate | [% by wt.] | — | — | — | 1 | 1 | 1 | 1 | — | — | — | — | — |
| Zinc oxide | [% by wt.] | — | — | — | — | — | — | — | 1 | 1 | — | — | — |
| Zinc hydroxystannate | [% by wt.] | — | — | — | — | — | — | — | — | — | 1 | — | — |
| Zinc stearate | [% by wt.] | — | — | — | — | — | — | — | — | — | — | 1 | — |
| Glass fibers 1 | [% by wt.] | — | — | — | — | — | — | — | — | — | — | — | — |
| Glass fibers 2 | [% by wt.] | 30 | 30 | 30 | 30 | 30 | 30 | 30 | 30 | 30 | 30 | 30 | 25 |
| Modulus of elasticity | [N/mm2] | 11500 | — | — | — | 9100 | 9500 | 11800 | 10100 | — | — | — | — |
| UL 94 classification | [—] | V-0 | V-0 | V-2 | V-0 | V-0 | V-0 | V-0 | V-0 | V-0 | V-0 | V-2 | V-0 |

The invention claimed is:

1. A diorganylphosphinic salt of the formula (I) a diorganyldiphosphinic salt of the formula (II), a polymer of the diorganylphosphinic salt of the formula (I), a polymer of the diorganyldiphosphinic salt of the formula (II), or a mixture thereof

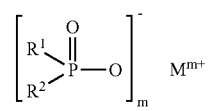

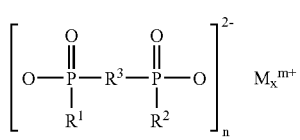

where
- $R^1$ and $R^2$ are identical or different and are $C_1$-$C_6$-alkyl, linear or branched, or aryl;
- $R^3$ is $C_1$-$C_{10}$-alkylene, linear or branched, $C_6$-$C_{10}$-arylene, -alkylaryiene, or -alkylarylene;
- M is Mg, Ca, Al, Sb, Sn, Ge, Ti, Fe, Zr, Zn, Ce, Bi, Sr, Mn, Li, Na, K, a protonated nitrogen base or a mixture thereof;
- m is from 1 to 4;
- n is from 1 to 4;
- x is from 1 to 4, wherein there is at least one partially water-soluble, ionizable compound, wherein the total content of at least one partially water-soluble, ionizable compound and the water-soluble content of the at least one partially water-soluble, ionizable compound is from 8200 to 100 ppm, wherein the at least one partially water-soluble, compound is a sulfate and wherein the total content of sulfate is from 3800 to 100 ppm, and the content of water-soluble sulfate is from 1200 to 10 ppm.

2. The diorganylphosphinic salt of the formula (I), a diorganyldiphosphinic salt of the formula (II), a polymer of the diorganylphosphinic salt of the formula (I), a polymer of the diorganyldiphosphinic salt of the formula (II), or a mixture thereof as claimed in one claim 1, wherein M is aluminum, calcium, titanium, zinc, tin or zirconium.

3. The diorganylphosphinic salt of the formula (I), a diorganyldiphosphinic salt of the formula (II), a polymer of the diorganylphosphinic salt of the formula (I), a polymer of the diorganyldiphosphinic salt of the formula (II), or a mixture thereof as claimed in claim 1, wherein $R^1$ and $R^2$ are identical or different, and are selected from the group consisting of methyl, ethyl, n-propyl, isopropyl, n-butyl, tert-butyl, n-pentyl, and phenyl.

4. The diorganylphosphinic salt of the formula (I), a diorganyldiphosphinic salt of the formula (II), a polymer of the diorganylphosphinic salt of the formula (I), a polymer of the diorganyldiphosphinic salt of the formula (II), or a mixture thereof as claimed in claim 1, wherein $R^3$ is methylene, ethylene, n-propylene, isopropylene, n-butylene, tert-butylene, n-pentylene, n-octylene, n-dodecylene, phenylene, naphthylene, methylphenylene, ethylphenylene, tert-butylphenylene, methylnaphthylene, ethylnaphthylene, tert-butylnaphthylene, phenylmethylene, phenylethylene, phenylpropylene, or phenylbutylene.

5. The diorganylphosphinic salt of the formula (I), a diorganyldiphosphinic salt of the formula (II), a polymer of the diorganyiphosphinic salt of the formula (I), a polymer of the diorganyldiphosphinic salt of the formula (II), or a mixture thereof as claimed in claim 1 wherein the diorganylphosphinic salt of the formula (I) is selected from the group consisting of aluminum trisdiethylphosphinate, aluminum trismethylethylphosphinate, aluminum trisdiphenylphosphinate, zinc bisdiethylphosphinate, zinc bismethylethylphosphinate, zinc bisdiphenylphosphinate, titanyl bisdiethylphosphinate, titanium tetrakisdiethylphosphinate, titanyl bismethylethylphosphinate, titanium tetrakismethylethylphosphinate, titanyl bisdiphenylphosphinate, titanium tetrakisdiphenylphosphinate and mixtures thereof.

6. The diorganylphosphinic salt of the formula (I), a diorganyldiphosphinic salt of the formula (II), a polymer of the diorganylphosphinic salt of the formula (I), a polymer of the diorganyldiphosphinic salt of the formula (II), or a mixture thereof as claimed in claim 1, having a residual moisture level from 0.01 to 10% by weight.

7. The diorganylphosphinic salt of the formula (I), a diorganyldiphosphinic salt of the formula (II), a polymer of the diorganylphosphinic salt of the formula (I), a polymer of the diorganyldiphosphinic salt of the formula (II), or a mixture thereof as claimed in claim 1, wherein the particle size of the diorganylphosphinic salt of formula (I) or the diorganylphosphinic salt of formula (II) is from 0.1 to 1000 μm.

8. The diorganylphosphinic salt of the formula (I), a diorganyldiphosphinic salt of the formula (II), a polymer of the diorganylphosphinic sait of the formula (I), a polymer of the diorganyldiphosphinic salt of the formula (II), or a mixture thereof as claimed in claim 1, having a bulk density from 80 to 800 g/l.

9. The diorganylphosphinic salt of the formula (I), a diorganyldiphosphinic salt of the formula (II), a polymer of the diorganylphosphinic salt of the formula (I), a polymer of the diorganyldiphosphinic salt of the formula (II), or a mixture thereof, as claimed in claim 1, having a solubility in at least one of water or organic solvents of from 0.001 to 10% by weight.

10. A process for preparation of diorganylphosphinic salt of the formula (I), a diorganyldiphosphinic salt of the formula (II), a polymer of the diorganylphosphinic salt of the formula (I), a polymer of the diorganyldiphosphinic salt of the formula (II), or a mixture thereof as claimed in claim 1, comprising the steps of reacting the diorganylphosphinic acid
   a) with a free base, or
   b) with the elemental metal of the desired cation, or
   c) in its alkali metal salt form, with a salt of the desired cation, or
   d) in the form of a reactive derivative, with a derivative of the desired cation for from 0.01 to 1 hours at from 0 to 300° C.

11. The process as claimed in claim 10, wherein the free base is a nitrogen base.

12. The process as claimed in claim 10, wherein the free base is selected from the group consisting of an oxide, mixed metal oxide hydroxide, hydroxide, carbonate, hydroxide carbonate, and hydrogencarbonate of the desired cation.

13. The process as claimed in claim 10, wherein the desired cation is selected from the group consisting of Mg, Ca, Al, Sb, Sn, Ge, Ti, Fe, Zr, Zn, Ce, Bi, Sr, Mn, Li, Na, and K.

14. The process as claimed in claim 1, wherein the salt of the desired cation comprises a compound having inorganic anions of the seventh main group of the periodic system of elements, having anions of the oxo acids of the seventh main group, having anions of the sixth main group, having anions of the oxo acids of the sixth main group, having anions of the fifth main group, having anions of the oxo acids of the fifth main group, having anions of the oxo acids of the fourth main group, having anions of the oxo acids of the third main group, having anions of the pseudohalides or having anions of the oxo acids of the transition metals.

15. The process as claimed in claim 10, wherein the salt of the desired cation comprises a compound having organic anions from the group of the mono-, di-, oligo-, or polycarboxylic acids, of acetic acid, of trifluoroacetic acid, propionates, butyrates, valerates, caprylates, oleates, stearates, of oxalic acid, of tartaric acid, citric acid, benzoic acid, salicylates, lactic acid, acrylic acid, maleic acid, succinic acid, of amino acids, of acidic hydroxy functions, para-phenolsulfonates, para-phenolsulfonate hydrates, acetylacetonate hydrates, tannates, dimethyldithiocarbamates, trifluoromethanesulfonate, alkylsulfonates, or aralkylsulfonates.

16. The process as claimed in claim 10, wherein the salt of the desired cation comprises a compound having anions from monoorganylphosphinates.

17. The process as claimed in claim 10, wherein the salt of the desired cation comprises a compound having anions from monoorganylphosphonates.

18. The process as claimed in claim 10, wherein the salt of the desired cation comprises a salt of protonated nitrogen base.

19. The process as claimed in claim 10, wherein the reactive derivative is selected from the group consisting of diorganylphosphinic esters, diorganylphosphinic pyroesters, diorganylphosphinic chlorides, diorganylphosphinic phosphates, diorganylphosphinic acetates, diorganylphosphinic phenolates, and mixtures thereof.

20. The process as claimed in claim 10, further comprising the step freeing the diorganylphosphinic salt from ancilliary components by washing with wash solvents, and removing the ancilliary components by solid-liquid separation.

21. A flame retardant composition comprising at least one compound selected from the group consisting of a diorganylphosphinic salt of the formula (I), a diorganyldiphosphinic salt of the formula (II), a polymer of the diorganylphosphinic salt of the formula (I), a polymer of the diorganyldiphosphinic salt of the formula (II), or a mixture thereof, as claimed in claim 1.

22. The flame retardant composition as claimed in claim 21, further comprising from 50 to 99.9% by weight of the at least one compound and from 0.1 to 50% by weight of at least one additive.

23. The flame retardant composition as claimed in claim 21, further comprising from 95 to 70% by weight of the at least one compound and from 5 to 30% by weight of at least one additive.

24. The flame retardant composition as claimed in claim 22, wherein the at least one additive is selected from the group consisting of melamine phosphate, dimelamine phosphate, pentamelamine triphosphate, trimelamine diphosphate, tetrakismelamine triphosphate, hexakismelamine pentaphosphate, melamine diphosphate, melamine tetraphosphate, melamine pyrophosphate, melamine polyphosphate, melam polyphosphate, melem polyphosphate, and melon polyphosphate.

25. The flame retardant composition as claimed in claim 22, wherein the at least one additive is selected from the group consisting of oligomeric esters of tris(hydroxyethyl) isocyanurate with aromatic polycarboxylic acids, benzoguanamine, tris(hydroxyethyl) isocyanurate, allantoin, glycoluril, melamine, melamine cyanurate, urea cyanurate, dicyandiamide, and guanidine.

26. The flame retardant composition as claimed in claim 22, wherein the at least one additive is selected from the group consisting of zinc compounds.

27. The flame retardant composition as claimed in claim 22, wherein the at least one additive is selected from the group consisting of carbodiimides (poly)isocyanates, e and mixtures thereof.

28. The flame retardant composition as claimed in claim 21, having an average particle size of from 0.1 to 3000 μm.

29. The flame retardant composition as claimed in claim 21, having a residual moisture level of from 0.01 to 10% by weight.

30. A flame-retardant polymer molding composition comprising at least one polymer and at least one compound selected from the group consisting of a diorganylphosphinic salt of the formula (I), a diorganyldiphosphinic salt of the formula (II), a polymer of the diorganylphosphinic salt of the formula (I), a polymer of the diorganyldiphosphinic salt of the formula (II), or a mixture thereof as claimed in claim 1.

31. The flame-retardant polymer molding composition as claimed in claim 30, wherein the flame-retardant polymer molding composition further comprises from 1 to 50% by weight of the at least one compound, and from 1 to 99% by weight of the at least one polymer.

32. The flame-retardant polymer molding composition as claimed in claim 30, further comprising from 1 to 50% by weight of the at least one compound, from 1 to 99% by weight of the at least one polymer, and from 0.1 to 60% by weight of at least one additive.

33. The flame-retardant polymer molding composition as claimed in claim 30, further comprising from 5 to 30% by weight of the at least one compound, from 5 to 90% by weight of the at least one polymer, and from 5 to 40% by weight of at least one additive.

34. The flame-retardant polymer molding composition as claimed in claim 31, wherein the at least one polymer is selected from the group consisting of thermoplastic polymers, thermoset polymers and mixtures thereof.

35. The flame-retardant polymer molding composition as claimed in claim 31, wherein the at least one polymer is selected from the group polybutylene terephthalates and the flame-retardant polymer molding composition has an SV value of from 750 to 1400, preferably from 850 to 1250.

36. The flame-retardant polymer molding composition as claimed in claim 31, wherein the at least one polymer is selected from the group consisting of nylon-6,6 polymers, wherein the flame-retardant polymer molding composition includes glass fibers and wherein the MVR value of the flame-retardant polymer molding composition is from 2 to 200 $cm^3$/min at 275° C, and 5 kg.

37. A process for producing the flame-retardant polymer molding composition as claimed in claim 31, comprising the steps of mixing the mixing the at least one compound with pellets of the at least one polymer and, optionally, with at least one additive in a mixer to form a mixture, homogenizing the mixture in a compounding assembly at relatively high temperatures to form a homogenized polymer strand, drawing the homogenized polymer strand off, cooling the homogenized polymer strand, and dividing the homogenized polymer strand.

38. A flame-retardant polymer article comprising at least one polymer and at least one compound selected from the group consisting of a diorganylphosphinic salt of the formula (I), a diorganyldiphosphinic salt of the formula (II), a polymer of the diorganylphosphinic salt of the formula (I), a polymer of the diorganyldiphosphinic salt of the formula (II), or a mixture thereof as claimed in claim 1, wherein the polymer article is in the form of a polymer film, polymer filament, or a polymer fiber.

39. The flame-retardant polymer article as claimed in claim 38, further comprising from 1 to 50% by weight of at least one compound, from 1 to 99% by weight of the at least one polymer, from 0 to 60% by weight of at least one additive, and from 0 to 60% by weight of at least one of a filler or a reinforcing material.

40. The flame-retardant polymer article as claimed in claim 38, further comprising from 1 to 50% by weight of at least one compound, from 1 to 99% by weight of the at least one polymer, from 0.1 to 60% by weight of at least one additive, and from 0.1 to 60% by weight of at least one of a filler or a reinforcing material.

41. The flame-retardant polymer article as claimed in claim 38, further comprising from 1 to 70% by weight of the at least one compound, from 1 to 99% by weight of the at least one polymer, from 0.1 to 60% by weight of at least one additive, and from 0.1 to 60% by weight of at least one of a filler or a reinforcing material.

42. The flame-retardant polymer article as claimed in claim 38, further comprising from 1 to 70% by weight of the at least one compound, from 1 to 99% by weight of the at least one polymer, from 0.1 to 60% by weight of at least one additive, and from 0.1 to 60% by weight of at least one of a filler or a reinforcing material.

43. The flame-retardant polymer article as claimed in claim 38, wherein the at least one polymer is a polybutylene terephthalate, and the modulus of elasticity of the flame-retardant polymer article is from 10 000 to 12 000 N/mm$^2$.

44. The flame-retardant polymer article as claimed in claim 38, wherein the at least one polymer is a nylon-6,6 polymer, and the modulus of elasticity of the flame-retardant polymer article is from 10 000 to 12 000 N/mm$^2$.

45. The flame-retardant polymer article as claimed in claim 38, wherein the at least one polymer is a nylon-6 polymer, and the modulus of elasticity of the flame-retardant polymer article is from 10 000 to 12 000 N/mm$^2$.

46. The diorganylphosphinic salt of the formula (I), a diorganyldiphosphinic salt of the formula (II), a polymer of the diorganylphosphinic salt of the formula (I), a polymer of the diorganyldiphosphinic salt of the formula (II), or a mixture thereof, as claimed in claim 1, wherein the water-soluble content of the at least one partially water-soluble, ionizable compound is from 2000 to 40 ppm.

47. The diorganylphosphinic salt of the formula (I), a diorganyldiphosphinic salt of the formula (II), a polymer of the diorganylphosphinic salt of the formula (I), a polymer of the diorganyldiphosphinic salt of the formula (II), or a mixture thereof, as claimed in claim 1, wherein the at least one partially water-soluble, ionizable compound is sulfate, wherein the total content of sulfate is from 2500 to 200 ppm, and the content of water-soluble sulfate is from 750 to 50 ppm.

48. The diorganylphosphinic salt of the formula (I), a diorganyldiphosphinic salt of the formula (II), a polymer of the diorganylphosphinic salt of the formula (I), a polymer of the diorganyldiphosphinic salt of the formula (II), or a mixture thereof, as claimed in claim 1, wherein the total content of sulfate is from 1000 to 300 ppm.

49. The diorganylphosphinic salt of the formula (I), a diorganyldiphosphinic salt of the formula (II), a polymer of the diorganylphosphinic salt of the formula (I), a polymer of the diorganyldiphosphinic salt of the formula (II), or a mixture thereof as claimed in claim 1, having a residual moisture level from 0.1 to 1% by weight.

50. The diorganylphosphinic salt of the formula (I), a diorganyldiphosphinic salt of the formula (II), a polymer of the diorganylphosphinic salt of the formula (I), a polymer of the diorganyldiphosphinic salt of the formula (II), or a mixture thereof, as claimed in claim 1, wherein the particle size of the diorganylphosphinic salt of formula (I) or the diorganylphosphinic salt of formula (II) is from 10 to 100 μm.

51. The diorganylphosphinic salt of the formula (I), a diorganyldiphosphinic salt of the formula (II), a polymer of the diorganylphosphinic salt of the formula (I), a polymer of the diorganyldiphosphinic salt of the formula (II), or a mixture thereof as claimed in claim 1, having a bulk density from 200 to 700 g/l.

52. The process as claimed in claim 11, wherein the nitrogen base is selected from the group consisting of ammonia, primary, secondary, tertiary, or quaternary amines, melamine, urea, biuret, guanidine, alkylguanidine, arylguanidine, diphenylguanidine, biguanide, biuret, allantoin, acetoguanamine, benzoguanamine, tolyltriazole, benzotriazole, 2-amino-4-methylpyrimidine, benzylurea, ethylenedimelamine, acetyleneurea, hydantoin, malonamide amidine, dimethylurea, 5,5-diphenylhydantoin, N,N'-diphenylurea, ethylenebis-5-triazone, glycine anhydride, tetramethylurea, triethanolamine, and condensates of melamine.

53. The process as claimed in claim 10, wherein the desired cation is selected from the group consisting of Al, Ca, Ti, Zn, Sn and Zr.

54. The flame retardant composition as claimed in claim 21, having an average particle size of from 0.1 to 1000 μm.

55. The flame retardant composition as claimed in claim 21, having an average particle size of from 1 to 100 μm.

56. The flame retardant composition as claimed in claim 21, having a residual moisture level of from 0.1 to 1% by weight.

57. The flame-retardant molding composition as claimed in claim 30, wherein the flame-retardant polymer molding composition has an SV value of from 850 to 1250.

* * * * *